(12) United States Patent
Baker et al.

(10) Patent No.: US 7,425,533 B2
(45) Date of Patent: Sep. 16, 2008

(54) MODIFIED HIRUDIN PROTEINS AND T-CELL EPITOPES IN HIRUDIN

(75) Inventors: Matthew Baker, Cambridge (GB); John Watkins, Cambridge (GB)

(73) Assignee: Merck Patent GmbH, Darmstadt (DE)

( * ) Notice: Subject to any disclaimer, the term of this patent is extended or adjusted under 35 U.S.C. 154(b) by 39 days.

(21) Appl. No.: 10/560,918

(22) PCT Filed: Jun. 25, 2004

(86) PCT No.: PCT/EP2004/006943

§ 371 (c)(1),
(2), (4) Date: Dec. 16, 2005

(87) PCT Pub. No.: WO2004/113386

PCT Pub. Date: Dec. 29, 2004

(65) Prior Publication Data

US 2006/0140929 A1     Jun. 29, 2006

(30) Foreign Application Priority Data

Jun. 26, 2003    (EP) .................................. 03014332

(51) Int. Cl.
*C07K 14/00* (2006.01)

(52) U.S. Cl. .......................................... 514/2; 530/300
(58) Field of Classification Search .................. 530/300; 514/2
See application file for complete search history.

(56) References Cited

U.S. PATENT DOCUMENTS 5,256,559 A * 10/1993 Maraganore et al. .......... 514/12
5,705,355 A *  1/1998 Tolstoshev et al. ............ 435/13

FOREIGN PATENT DOCUMENTS

EP        0 468 448       *  1/1992

OTHER PUBLICATIONS

Scharf et al., 1989; Primary structures of new 'iso-hirudins'. FEBS Letters 255 (1): 105-110.*
Schlaeppi et al. 1990; Preparation of monoclonal antibodies to hirudin and hirudin peptides. European Journal of Biochemistry 188: 463: 470.*

* cited by examiner

Primary Examiner—Karen Cochrane Carlson
(74) Attorney, Agent, or Firm—Olson & Cepuritis, Ltd.

(57) ABSTRACT

Modified forms of hirudin having improved properties are disclosed. The modified hirudin compounds are hirudin variants comprising amino acid substitutions in the sequence of hirudin. Peptide molecules consisting of the amino acid residue sequence CILGSDGEKNQCVTGEGTPK-PESHNDGDFE (SEQ ID NO: 1) or a sequence consisting of at least 9 consecutive amino acid residues of SEQ ID NO: 1 having a potential MHC class II binding activity are disclosed. The peptide has a stimulation index of >1.8 in a biological assay of cellular proliferation, in which the index is defined as the value of cellular proliferation scored following stimulation by the peptide and divided by the value of cellular proliferation scored in control cells that have not been exposed to the peptide.

2 Claims, 6 Drawing Sheets

Figure 1

```
                                                       RH
                                                       AA
VVYTDCTESG QNLCLCEGSN VCGQGNKCIL GSDGEKNQCV TGEGTPKPES HNDGDFEEIP EEYLQ
1          11         21         31         41         51         61    65
```

Figure 3

MODIFIED HIRUDIN PROTEINS AND T-CELL EPITOPES IN HIRUDIN

This application is the National Stage of International Application No. PCT/EP2004/006943, filed on Jun. 25, 2004. This application claims priority benefit of European Patent Application No. 03014332.5, filed on Jun. 26, 2003.

FIELD

The invention concerns hirudin and in particular modified forms of hirudin with improved properties. The improved proteins contain amino acid substitutions at specific positions. The invention provides modified hirudin with improved biological activity concomitant with reduced immunogenic potential in the protein. The improved proteins are intended for therapeutic use in the treatment of diseases in humans.

BACKGROUND

Native hirudin constitutes a group of nearly identical polypeptides with a molecular weight around 7000 Daltons and consisting of 65 to 66 amino acids that are produced in the salivary glands of the leech *Hirudo medicinalis* [Markwardt F (1970) Methods in Enzymology; 19: 924-932]. Hirudin is the most potent natural inhibitor of the serine protease thrombin, with a Ki of $10^{-11}$ to $10^{-14}$ M. It forms a 1:1 complex at the active site of thrombin resulting in inhibition of its proteolytic activity [Johnson P H, et al (1989) Sem. Thromb. Hemost.; 15: 320-315; Stone S R, & Hofsteenge J. (1986) Biochemistry; 4622-46242,3]. The X-ray crystal structure of hirudin and the hirudin/thrombin complex have been solved. The globular N-terminal domain of hirudin binds to the active-site cleft of thrombin, while the C-terminal tail binds to the fibrinogen binding exosite of thrombin. Site directed mutagenesis studies have been carried out with both hirudin and the hirudin/thrombin complex [Grütter M G et al (1990) *EMBO Journal;* 9: 2361-2365; Rydel T J, et al (1990) *Science;* 249:277-280; Rydel T J, et al (1991) *Journal of Molecular Biology;* 221: 583-601].

Recombinant hirudins (r-hirudin) differ from naturally occurring hirudin by the lack of a sulphate group at tyrosine 63 and the first two N-terminal amino acids [Märki W E, et al (1997) *Semin. Thromb. Haemost;* 17: 88-93]. Preclinical and clinical studies have shown that r-hirudin is an effective anticoagulant for prevention and treatment of venous thromboembolism in patients undergoing elective hip surgery and for patients with chronic stable coronary heart disease, acute myocardial infarction, unstable angina pectoris as an adjunct to coronary angioplasty, and in combination with intracoronary thrombolysis [Lieber V, et al (2002) *Seminars in Thrombosis and Hemostasis;* 28: 483-489]. Recent studies have also suggested that hirudin could be used in stroke therapy [Karabiyikoglu M, et al (2004) *Journal of Cerebral Blood Flow & Metabolism.* 24: 159-166].

The therapeutic potential of hirudin based thrombin inhibitors has been demonstrated by the development of Desirudin [Iprivask, Aventis Inc.]; [Val$^1$, Val$^2$]-63-desulphohirudin and Lepirudin [Refludan, Schering/Berlex]; [Leu$^1$, Thr$^2$]-63-desulphohirudin.

Desirudin was first approved in the EU for thrombosis prophylaxis after orthopaedic hip and knee surgery. In April 2003 it was approved by the FDA and is now marketed as Iprivask. Lepirudin is approved in both the European Union (1997) and the United States (1998) for the treatment of patients suffering from heparin-induced thrombocytopaenia (HIT) [Greinacher A, et al (1999). *Circulation;* 99: 73-80; Greinacher A, Janssens U, Berg G et al. (1999) *Circulation;* 99: 587-593; Harenberg J, et al (1997) *Seminars in Thrombosis and Hemostasis;* 23: 189-196]. Heparin is currently used to prevent blood clots in more than 20 million patients per year in Europe and the US. In the US and EU alone, approximately 500,000 patients per year are potential candidates for lepirudin therapy.

Despite its evident clinical utility, a significant problem associated with the clinical use of hirudin is its immunogenicity. Anti-hirudin antibodies can be detected in patients who have received lepirudin and desirudin [Song X, et al (1999) *Circulation;* 100: 1528-1532; Eichler P, et al (2000) *Blood;* 96: 2373-2378; Greinacher A, et al (2003) *Blood;* 101: 2617-2619; Kischer K-G, et al (2003) *Thromb. Haemost;* 89: 973-982; Eichler P, et al (2004) *Blood;* 103: 613-616]. Moreover, lepirudin can cause fatal anaphylaxis, particularly in HIT patients who are treated within 3 months of a previous exposure. Between 1994 and 2002, 9 patients have been judged to have had severe anaphylaxis in close temporal contact with lepirudin. All reactions occurred within minutes of intravenous lepirudin administration, with 4 fatal outcomes. In all 4 cases, a previous uneventful treatment course with lepirudin was identified (1 to 12 weeks earlier). High-titre IgG anti-lepirudin antibodies were recorded in an additional patient with anaphylaxis [Greinacher A, Lubenow N, Eichler P (2003). *Circulation;* 108: 2062-2065].

Generation of a high affinity long lived antibody response, and in particular a response that can be seen to have undergone class switching to high titre IgG antibody, is dependent on CD4+ T-cell help. T cell receptor (TCR) binding of peptide epitopes presented in the context of MHC Class II on the surface of antigen presenting cells (APCs), will lead to T-cell proliferation and the production of cytokines that can modulate immune responses. Patients who develop antibodies to hirudin☐ have T-cells that are capable of recognising peptide fragments of hirudin bound to MHC class II molecules.

The present invention is concerned with the identification of T-cell epitopes in hirudin and with hirudin molecules in which amino acid substitution and or combinations of substitution have been conducted. The substitutions confer a reduced immunogenic profile on the protein whilst retaining functional activity.

SUMMARY OF THE INVENTION

The invention provides hirudin molecules containing amino acid substitutions. The amino acid substitutions confer improved properties to the protein. The improved properties concern the immunogenic properties of the protein.

The molecules of the invention have new properties. Such molecules may cause benefit for a patient in need of anticoagulation therapy or prophylaxis.

The molecules of the invention are characterised by the protein sequences defined herein as M 1-81.

The molecules of the invention are further characterised their relative activity in a thrombin inhibition assay of between around 0.2 and around 3.3.

The most preferred molecules of the invention is characterised by the protein sequences M1 and M2 and are further characterised by a relative activity of around 1.2-1.4 in a thrombin inhibition assay.

The most preferred molecules of the invention are characterised yet further still by comprising sequences demonstrated to show reduced immunogenicity in human cells. In particular reduced immunogenicity as measured using a "T-cell assay" or a "time course assay" as defined herein.

The present invention provides for modified forms of hirudin proteins that are expected to display enhanced properties in vivo. The present invention discloses the major regions of the hirudin primary sequence that are immunogenic in man and provides modification to the sequences to eliminate or reduce the immunogenic effectiveness of these sites.

In one embodiment, synthetic peptides comprising the immunogenic regions can be provided in pharmaceutical composition for the purpose of promoting a tolerogenic response to the whole molecule.

In a further embodiment, the modified hirudin molecules of the present invention can be used in pharmaceutical compositions.

In summary the invention is concerned with the following issues:

A modified hirudin molecule having the biological activity of hirudin yet containing one or more amino acid substitutions;

an accordingly specified molecule, wherein said amino acid substitutions are conducted within the sequence (A) below comprising T-cell epitopes wherein;
(A)=CILGSDGEKNQCVTGEGTPKPESHNDGDFE (SEQ ID NO: 1);

an accordingly specified molecule, wherein said originally present T-cell epitope sequence (A) comprises MHC class II ligands or peptide sequences which show the ability to stimulate or bind T-cells via presentation on class II;

a peptide sequence consisting of at least 9 consecutive amino acid residues as derived from sequence (A) above and its use for the manufacture of a hirudin like molecule having substantially no or less immunogenicity than any non-modified molecule and having the biological activity of hirudin when used in vivo;

a pharmaceutical composition comprising 9 or more consecutive residues from the peptide sequence (A) above;

a modified hirudin molecule having the biological activity of hirudin and comprising one or more amino acid substitutions as specified above or below;

a modified hirudin molecule having the biological activity of hirudin and comprising at least the amino acid substitutions in SEQ ID NO: 3: I29A and L30A;

a modified hirudin molecule having the biological activity of hirudin and comprising at least the amino acid substitutions in SEQ ID NO: 3: I29R and L30H;

a modified hirudin molecule of structure (M; SEQ ID NO: 2):

```
V V Y T D C T E S G Q N X¹ C X² C E G S V X³ C G Q
G N K C X⁴ X⁵ G S D G E K N Q C X⁶ T G E G T P X⁷
X⁸ E S H N X⁹ G D X¹⁰ E E I P E E Y L Q
``` wherein;

$X^1$=T or L $X^2$=T or A or H or Q or T or L;

$X^3$=A or G or H or K or N or P or Q or R or V;

$X^4$=A or D or E or G or H or K or N or Q or R or S or T or I;

$X^5$=A or D or E or G or H or K or N or P or Q or R or S or T or L;

$X^6$=A or T or V;

$X^7$=T or K;

$X^8$=A or T or P;

$X^9$=E or N or R or D;

$X^{10}$=H or F and whereby $X^1$=L, $X^2$=L, $X^3$=V, $X^4$=I, $X^5$=L, $X^6$=V, $X^7$=K, $X^8$=P, $X^9$=D and $X^{10}$=F are simultaneously excluded.

The mutant proteins of the present invention are readily made using recombinant DNA techniques well known in the art and the invention provides methods for the recombinant production of such molecules.

In as far as this invention relates to modified hirudin, compositions containing such modified hiridin proteins or fragments of modified hirudin proteins and related compositions should be considered within the scope of the invention. In another aspect, the present invention relates to nucleic acids encoding modified hirudin entities. In a further aspect the present invention relates to methods for therapeutic treatment of humans using the modified hirudin.

DETAILED DESCRIPTION OF THE INVENTION

In nature, the mature hirudin protein is polypeptide of 65 to 66 amino acids. The amino acid sequence of a wild type (WT) hirudin (depicted as single-letter code) is as follows (M82):

```
V V Y T D C T E S G Q N L C L C E G S V V C G Q G
N K C I L G S D G E K N Q C V T G E G T P K P E S
H N D G D F E E I P E E Y L Q (SEQ ID NO: 3)
```

The term "hirudin" is used herein to denote recombinant or synthetic equivalents of the above sequence which are in turn analogues of the native hirudin proteins constituting a group of nearly identical polypeptides with a molecular weight around 7000 Daltons and which are produced in the salivary glands of the leech *Hirudo medicinalis*. In some instances the term is also used more broadly herein to include modified hirudin proteins or more especially a hirudin mutein.

The term "mutein" is used herein to denote a hirudin protein engineered to contain one or more amino acid substitutions differing from the above native sequence.

The term "peptide" as used herein, is a compound that includes two or more amino acids. The amino acids are linked together by a peptide bond.

A peptide bond is the sole covalent linkage between amino acids in the linear backbone structure of all peptides, polypeptides or proteins. The peptide bond is a covalent bond, planar in structure and chemically constitutes a substituted amide. An "amide" is any of a group of organic compounds containing the grouping —CONH—.

There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins.

Each different arrangement of amino acids forms different polypeptides or proteins. The number of polypeptides—and hence the number of different proteins—that can be formed is practically unlimited.

Since the peptide bond is the sole linkage between amino acids, all peptides, polypeptides or proteins have defined termini conventionally referred to as the "N-terminus" or "N-terminal" residue and the "C-terminus" or "C-terminal" residue". The N-terminal residue bears a free amino group, whereas the C-terminal residue bears a free carboxyl group.

The term "T-cell epitope" means according to the understanding of this invention an amino acid sequence which is able to bind MHC class II, able to stimulate T-cells and/or also to bind (without necessarily measurably activating) T-cells in complex with MHC class II. In principle such an amino acid sequence can be not less than 9 residues in length but typically will be 10 or 11 or 12 or 13 or 14 or 15 or more residues in length.

Reference to "substantially non-immunogenic" or "reduced immunogenic potential" includes reduced immunogenicity compared to a parent protein or to a fusion protein containing the wild-type (WT) or native amino acid sequences of the test moiety.

The term "immunogenicity" includes an ability to provoke, induce or otherwise facilitate a humoral and or T-cell mediated response in a host animal and in particular where the "host animal" is a human.

The terms "T-cell assay" and "immunogenicity assay" concern ex vivo measures of immune reactivity. As such these involve a test immunogen e.g. a protein or peptide being brought into contact with live human immune cells and their reactivity measured. A typical parameter of induced reactivity is proliferation. The presence of suitable control determinations are critical and implicit in the assay.

"Time course assay" refers to a biological assay such as a proliferation assay in which determinations of activity are made sequentially over a period of time. In the present context, a "time course T-cell assay", refers to the determination of T-cell proliferation in response to a test immunogen (peptide) at multiple times following exposure to the test immunogen. The terms "time course T-cell assay" and "time course immunogenicity assay" may be used interchangeably herein.

One conventional way in which T-cell assays are expressed is by use of a "stimulation index" or "SI". The stimulation index (SI) is conventionally derived by division of the proliferation score (e.g. counts per minute of radioactivity if using for example $^3$H-thymidine incorporation) measured to a test immunogen such as a peptide by the score measured in cells not contacted with a test immunogen. Test immunogens (peptides) which evoke no response give SI=1.0 although in practice SI values in the range 0.8-1.2 are unremarkable. The inventors have established that in the operation of such immunogenicity assays, a stimulation index equal to or greater than 2.0 is a useful measure of significant induced proliferation.

PBMC means peripheral blood mononuclear cells in particular as obtained from a sample of blood from a donor. PBMC are readily isolated from whole blood samples using a density gradient centrifugation technique well understood in the art and comprise predominantly lymphocytes (B and T cells) and monocytes. Other cell types are also represented.

"Relative activity" means according the present context activity measured for a test protein in any single assay expressed relative to the activity measured for a positive control protein in an identical assay and usually conducted in parallel. Thus if the test protein and the control protein have the same measured activity the relative activity is said to be 1.

A "thrombin inhibition assay" according to the present context means an in vitro assay able to provide a reading of the functional capability of the test protein. In the present instance this means the ability of a given hirudin mutein to evoke a specific measurable chromogenic response. Particularly suitable assays are exemplified herein using thrombin and the chromogenic thrombin substrate H-D-Phe-Pep-Arg-pNA. Other assay formats can be contemplated to also provide quantitative estimations of specific activity of the test molecules and permit $ED_{50}$ determinations. Examples include the Activated Partial Thromboplastin Time coagulation (aPTT) assay and the Ecarin clotting time (ECT) assay, each well known in the art.

In another aspect, the present invention relates to nucleic acids encoding modified hirudin entities. Such nucleic acids are preferably comprised within an expression vector. The control sequence that are suitable for prokaryotes, for example, include a promoter, optionally an operator sequence, and a ribosome binding site. Eukaryotic cells are known to utilise promoters, enhancers and polyadenylation signals. Such nucleic acids in general comprise a selection means typically an additional gene encoding a protein able to provide for the survival of the host cell. An example of such a selection gene is the beta-lactamase gene suitable for some *E. coli* host cells and this and others are well known in the art ["Molecular Cloning: A Laboratory Manual", second edition (Sambrook et al., 1989); "Gene Transfer Vectors for Mammalian Cells" (J. M. Miller & M. P. Calos, eds., 1987); "Current Protocols in Molecular Biology" (F. M. Ausubel et al., eds., 1987)].

Nucleic acid is "operably linked" when it is placed into a functional relationship with another nucleic acid sequence. For example, DNA for a pre-sequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in the same reading frame. However, enhancers do not have to be contiguous. Linking is accomplished by ligation at convenient restriction sites. If such sites do not exist, the synthetic oligonucleotide adaptors or linkers are used in accordance with conventional practice.

In some embodiments the expression vector comprises a nucleic acid sequence encoding a hirudin variant operably linked to an expression control sequence. In various embodiments the expression vector comprises a nucleic acid sequence encoding a protein selected from the group comprising inclusively M1 to M81. Such an expression vector will comprise at least the hirudin encoding domain of one of the said proteins operably linked with suitable expression control and selection sequences. Such an expression vector would include degenerate versions of the nucleic acid wherein degeneracy in relation to polynucleotides refers to the fact well recognised that in the genetic code many amino acids are specified by more than one codon. The degeneracy of the code accounts for 20 different amino acids encoded by 64 possible triplet sequences of the four different bases comprising DNA.

Another aspect of the present invention is a cultured cell comprising at least one of the above-mentioned vectors.

A further aspect of the present invention is a method for preparing the modified hirudin comprising culturing the above mentioned cell under conditions permitting expression of the hirudin from the expression vector and purifying the hirudin from the cell.

Whilst the hirudin molecules of the invention and are readily made using the above described recombinant DNA based methods, it is recognised that as short polypeptides, the preferred molecules of the invention can be made by wholly synthetic means using solid phase chemical synthesis methods or equivalent techniques well known in the art [for review see Bruckdorfer, T. et al (2004) *Curr. Pharm. Biotechnol.* 5:29-43 and references therein].

In a yet further aspect, the present invention relates to methods for therapeutic treatment of humans using the hirudin compositions. For administration to an individual, any of the modified compositions would be produced to be preferably at least 80% pure and free of pyrogens and other contaminants. It is further understood that the therapeutic compositions of the hirudin proteins may be used in conjunction with a pharmaceutically acceptable excipient. The pharmaceutical compositions according to the present invention are prepared conventionally, comprising substances that are customarily used in pharmaceuticals, e.g. Remington's Pharmaceutical Sciences, (Alfonso R. Gennaro ed. 18$^{th}$ edition 1990), including excipients, carriers adjuvants and buffers. The compositions can be administered, e.g. parenterally, enterally, intramuscularly, subcutaneously, intravenously or other routes useful to achieve an effect. Conventional excipients include pharmaceutically acceptable organic or inorganic carrier substances suitable for parenteral, enteral and other routes of administration that do not deleteriously react with the agents. For parenteral application, particularly suitable are injectable sterile solutions, preferably oil or aqueous solutions, as well as suspensions, emulsions or implants, including suppositories. Ampules are convenient unit dosages. The pharmaceutical preparations can be sterilised and, if desired, mixed with stabilisers, wetting agents, emulsifiers, salts for influencing osmotic pressure, buffers or other substances that do not react deleteriously with the active compounds.

The major embodiments of the present invention are encompassed by the protein sequences M 1-81. A number of muteins show improved activity relative to the WT molecule (M82). All active muteins are embodiments of the invention.

The hirudin muteins of the present were constructed to be less immunogenic than the parental molecule. The design of individual muteins was directed from immunological considerations as well as functional activity data. A single major region of immunological importance within the molecule was defined using screening assays involving use of PBMC preparations from healthy donor subjects. This approach has proven to be a particularly effective method for the identification such biologically relevant immunogenic peptides and is disclosed herein as an embodiment of the invention. In the present study, the method has involved the testing of overlapping hirudin-derived peptide sequences in a scheme so as to scan and test the entire hirudin sequence. Such a scan required synthesis and use of 19 peptides each of 15 residues in length. The synthetic peptides were tested for ability to evoke a proliferative response in human T-cells cultured in vitro. Where this type of approach is conducted using naïve human T-cells taken from healthy donors, the inventors have established that a stimulation index equal to or greater than 2.0 is a useful measure of induced proliferation.

One significant epitope region (termed R1) was identified in these studies. R1 encompasses residues 28-57 of SEQ ID NO: 3 and comprises the sequence CILGSDGEKNQCVTGEGTPKPESHNDGDFE (SEQ ID NO: 1).

The R1 peptide sequence represents the critical information required for the construction of modified hirudin molecules in which the epitope is compromised. Equally, the R1 sequence represent the critical information required for the production of tolerogenic peptides. Epitope region R1 is an embodiment of the invention.

Under the scheme of the present, the epitopes are compromised by mutation to result in sequences no longer able to function as T-cell epitopes. It is possible to use recombinant DNA methods to achieve directed mutagenesis of the target sequences and many such techniques are available and well known in the art. Broadly, the hirudin muteins herein were constructed containing mutations within the immunogenic region R1. Individual residues were targeted based upon the known binding properties of HLA-DR molecules in that they have an almost exclusive preference for a hydrophobic amino acid in pocket 1 and that this is the most important determinant of peptide binding [Jardetzky, T. S. et al (1990), *EMBO J.* 9: 1797-1803; Hill, C. M. et al (1994) *J. Immunol.* 152: 2890-2898]. Exhaustive mutational analysis identified those residues both inside and outside R1 that could be altered without adversely affecting the activity of the fusion protein. A number of muteins show improved activity relative to the WT molecule. All active muteins are embodiments of the invention.

The general method of the present invention leading to the modified TPO comprises the following steps:

(a) determining the amino acid sequence of the polypeptide or part thereof;

(b) identifying one or more potential T-cell epitopes within the amino acid sequence of the protein by any method including determination of the binding of the peptides to MHC molecules using in vitro or in silico techniques or biological assays;

(c) designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays. Such sequence variants are created in such a way to avoid creation of new potential T-cell epitopes by the sequence variations unless such new potential T-cell epitopes are, in turn, modified in such a way to substantially reduce or eliminate the activity of the T-cell epitope; and (d) constructing such sequence variants by recombinant DNA techniques and testing said variants in order to identify one or more variants with desirable properties according to well known recombinant techniques.

Taken together, the inventors have been able to define modified hirudin proteins which can be depicted by the following structure (M; SEQ ID NO: 2):

V V Y T D C T E S G Q N X$^1$ C X$^2$ C E G S V X$^3$ C G Q
G N K C X$^4$ X$^5$ G S D G E K N Q C X$^6$ T G E G T P X$^7$
X$^8$ E S H N X$^9$ G D X$^{10}$ E E I P E E Y L Q wherein;
  X$^1$=T or L
  X$^2$=T or A or H or Q or T or L;
  X$^3$=A or G or H or K or N or P or Q or R or V;
  X$^4$=A or D or E or G or H or K or N or Q or R or S or T or I;
  X$^5$=A or D or E or G or H or K or N or P or Q or R or S or T or L;

$X^6$=A or T or V;
$X^7$=T or K;
$X^8$=A or T or P;
$X^9$=E or N or R or D;
$X^{10}$=H or F and whereby $X^1$=L, $X^2$=L, $X^3$=V, $X^4$=I, $X^5$=L, $X^6$=V, $X^7$=K, $X^8$=P, $X^9$=D and $X^{10}$=F are simultaneously excluded.

The following, figures, sequence listing and examples are provided to aid the understanding of the present invention. It is understood that modifications can be made in the procedures set fourth without departing from the spirit of the invention.

DESCRIPTION OF THE SEQUENCES

To aid the understanding of the invention, Table 1 below sets out a description of the hirudin muteins. The derivation and properties of these proteins are also more fully disclosed in the examples. In Table 1, the heading labeled "Substitution(s)" refers to substitutions in SEQ ID NO: 3.

TABLE 1

Description of the sequences

| M No | Substitution(s) | M No | Substitution(s) |
|---|---|---|---|
| M 1 | I29A L30A | M 42 | V21A |
| M 2 | I29R L30H | M 43 | V21G |
| M 3 | I29E L30K V40A | M 44 | V21H |
| M 4 | I29E L30K V40T | M 45 | V21K |
| M 5 | I29E L30K D53E | M 46 | V21N |
| M 6 | I29E L30K D53N | M 47 | V21P |
| M 7 | I29R L30K V40A | M 48 | V21Q |
| M 8 | I29R L30K V40T | M 49 | V21R |
| M 9 | I29R L30K D53E | M 50 | I29A |
| M 10 | I29R L30K D53N | M 51 | I29D |
| M 11 | I29R L30R V40T | M 52 | I29E |
| M 12 | I29A L30K | M 53 | I29G |
| M 13 | I29A L30Q | M 54 | I29H |
| M 14 | I29A L30R | M 55 | I29K |
| M 15 | I29A L30T | M 56 | I29N |
| M 16 | I29D L30A | M 57 | I29Q |
| M 17 | I29D L30Q | M 58 | I29R |
| M 18 | I29D L30R | M 59 | I29S |
| M 19 | I29E L30K | M 60 | I29T |
| M 20 | I29E L30Q | M 61 | L30A |
| M 21 | I29E L30R | M 62 | L30D |
| M 22 | I29E L30T | M 63 | L30E |
| M 23 | I29R L30K | M 64 | L30G |
| M 24 | I29R L30Q | M 65 | L30H |
| M 25 | I29R L30R | M 66 | L30K |
| M 26 | I29R L30T | M 67 | L30N |
| M 27 | I29S L30A | M 68 | L30P |
| M 28 | I29S L30K | M 69 | L30Q |
| M 29 | I29S L30Q | M 70 | L30R |
| M 30 | I29S L30R | M 71 | L30S |
| M 31 | I29S L30T | M 72 | L30T |
| M 32 | I29T L30A | M 73 | V40A |
| M 33 | I29T L30K | M 74 | V40T |
| M 34 | I29T L30Q | M 75 | K47T |
| M 35 | I29T L30R | M 76 | P48A |
| M 36 | I29T L30T | M 77 | P48T |
| M 37 | L13T | M 78 | D53E |
| M 38 | L15A | M 79 | D53N |
| M 39 | L15H | M 80 | D53R |
| M 40 | L15Q | M 81 | F56H |
| M 41 | L15T | M 82 | WT |

TABLE A

Sequences of modified (M1-M81) and wild-type hirudin (M82), and T-cell epitope containing region A within wild-type hirudin:

M 1 (SEQ ID NO: 4)
V V Y T D C T E S G Q N L C L C E G S V V C G Q G
N K C A A G S D G E K N Q C V T G E G T P K P E S
H N D G D F E E I P E E Y L Q

M 2 (SEQ ID NO: 5)
V V Y T D C T E S G Q N L C L C E G S V V C G Q G
N K C R H G S D G E K N Q C V T G E G T P K P E S
H N D G D F E E I P E E Y L Q

M 3 (SEQ ID NO: 6)
V V Y T D C T E S G Q N L C L C E G S V V C G Q G
N K C E K G S D G E K N Q C A T G E G T P K P E S
H N D G D F E E I P E E Y L Q

M 4 (SEQ ID NO: 7)
V V Y T D C T E S G Q N L C L C E G S V V C G Q G
N K C E K G S D G E K N Q C T T G E G T P K P E S
H N D G D F E E I P E E Y L Q

M 5 (SEQ ID NO: 8)
V V Y T D C T E S G Q N L C L C E G S V V C G Q G
N K C E K G S D G E K N Q C V T G E G T P K P E S
H N E G D F E E I P E E Y L Q

M 6 (SEQ ID NO: 9)
V V Y T D C T E S G Q N L C L C E G S V V C G Q G
N K C E K G S D G E K N Q C V T G E G T P K P E S
H N N G D F E E I P E E Y L Q

M 7 (SEQ ID NO: 10)
V V Y T D C T E S G Q N L C L C E G S V V C G Q G
N K C R K G S D G E K N Q C A T G E G T P K P E S
H N D G D F E E I P E E Y L Q

M 8 (SEQ ID NO: 11)
V V Y T D C T E S G Q N L C L C E G S V V C G Q G
N K C R K G S D G E K N Q C T T G E G T P K P E S
H N D G D F E E I P E E Y L Q

M 9 (SEQ ID NO: 12)
V V Y T D C T E S G Q N L C L C E G S V V C G Q G
N K C R K G S D G E K N Q C V T G E G T P K P E S
H N E G D F E E I P E E Y L Q

M 10 (SEQ ID NO: 13)
V V Y T D C T E S G Q N L C L C E G S V V C G Q G
N K C R K G S D G E K N Q C V T G E G T P K P E S
H N N G D F E E I P E E Y L Q

M 11 (SEQ ID NO: 14)
V V Y T D C T E S G Q N L C L C E G S V V C G Q G
N K C R R G S D G E K N Q C T T G E G T P K P E S
H N D G D F E E I P E E Y L Q

M 12 (SEQ ID NO: 15)
V V Y T D C T E S G Q N L C L C E G S V V C G Q G
N K C A K G S D G E K N Q C V T G E G T P K P E S
H N D G D F E E I P E E Y L Q

M 13 (SEQ ID NO: 16)
V V Y T D C T E S G Q N L C L C E G S V V C G Q G
N K C A Q G S D G E K N Q C V T G E G T P K P E S
H N D G D F E E I P E E Y L Q

M 14 (SEQ ID NO: 17)
V V Y T D C T E S G Q N L C L C E G S V V C G Q G
N K C A R G S D G E K N Q C V T G E G T P K P E S
H N D G D F E E I P E E Y L Q

M 15 (SEQ ID NO: 18)
V V Y T D C T E S G Q N L C L C E G S V V C G Q G
N K C A T G S D G E K N Q C V T G E G T P K P E S
H N D G D F E E I P E E Y L Q

TABLE A-continued

Sequences of modified (M1-M81) and wild-type hirudin (M82), and T-cell epitope containing region A within wild-type hirudin:

M 16 (SEQ ID NO: 19)
V V Y T D C T E S G Q N L C L C E G S V V C G Q G
N K C D A G S D G E K N Q C V T G E G T P K P E S
H N D G D F E E I P E E Y L Q

M 17 (SEQ ID NO: 20)
V V Y T D C T E S G Q N L C L C E G S V V C G Q G
N K C D Q G S D G E K N Q C V T G E G T P K P E S
H N D G D F E E I P E E Y L Q

M 18 (SEQ ID NO: 21)
V V Y T D C T E S G Q N L C L C E G S V V C G Q G
N K C D E G S D G E K N Q C V T G E G T P K P E S
H N D G D F E E I P E E Y Q

M 19 (SEQ ID NO: 22)
V V Y T D C T E S G Q N L C L C E G S V V C G Q G
N K C E K G S D G E K N Q C V T G E G T P K P E S
H N D G D F E E I P E E Y L Q

M 20 (SEQ ID NO: 23)
V V Y T D C T E S G Q N L C L C E G S V V C G Q G
N K C E Q G S D G E K N Q C V T G E G T P K P E S
H N D G D F E E I P E E Y L Q

M 21 (SEQ ID NO: 24)
V V Y T D C T E S G Q N L C L C E G S V V C G Q G
N K C E R G S D G E K N Q C V T G E G T P K P E S
H N D G D F E E I P E E Y L Q

M 22 (SEQ ID NO: 25)
V V Y T D C T E S G Q N L C L C E G S V V C G Q G
N K C E T G S D G E K N Q C V T G E G T P K P E S
H N D G D F E E I P E E Y L Q

M 23 (SEQ ID NO: 26)
V V Y T D C T E S G Q N L C L C E G S V V C G Q G
N K C R K G S D G E K N Q C V T G E G T P K P E S
H N D G D F E E I P E E Y L Q

M 24 (SEQ ID NO: 27)
V V Y T D C T E S G Q N L C L C E G S V V C G Q G
N K C R Q G S D G E K N Q C V T G E G T P K P E S
H N D G D F E E I P E E Y L Q

M 25 (SEQ ID NO: 28)
V V Y T D C T E S G Q N L C L C E G S V V C G Q G
N K C R R G S D G E K N Q C V T G E G T P K P E S
H N D G D F E E I P E E Y L Q

M 26 (SEQ ID NO: 29)
V V Y T D C T E S G Q N L C L C E G S V V C G Q G
N K C R T G S D G E K N Q C V T G E G T P K P E S
H N D G D F E E I P E E Y L Q

M 27 (SEQ ID NO: 30)
V V Y T D C T E S G Q N L C L C E G S V V C G Q G
N K C S A G S D G E K N Q C V T G E G T P K P E S
H N D G D F E E I P E E Y L Q

M 28 (SEQ ID NO: 31)
V V Y T D C T E S G Q N L C L C E G S V V C G Q G
N K C S K G S D G E K N Q C V T G E G T P K P E S
H N D G D F E E I P E E Y L Q

M 29 (SEQ ID NO: 32)
V V Y T D C T E S G Q N L C L C E G S V V C G Q G
N K C S Q G S D G E K N Q C V T G E G T P K P E S
H N D G D F E E I P E E Y L Q

M 30 (SEQ ID NO: 33)
V V Y T D C T E S G Q N L C L C E G S V V C G Q G
N K C S R G S D G E K N Q C V T G E G T P K P E S
H N D G D F E E I P E E Y L Q

M 31 (SEQ ID NO: 34)
V V Y T D C T E S G Q N L C L C E G S V V C G Q G
N K C S T G S D G E K N Q C V T G E G T P K P E S
H N D G D F E E I P E E Y L Q

M 32 (SEQ ID NO: 35)
V V Y T D C T E S G Q N L C L C E G S V V C G Q G
N K C T A G S D G E K N Q C V T G E G T P K P E S
H N D G D F E E I P E E Y L Q

M 33 (SEQ ID NO: 36)
V V Y T D C T E S G Q N L C L C E G S V V C G Q G
N K C T K G S D G E K N Q C V T G E G T P K P E S
H N D G D F E E I P E E Y L Q

M 34 (SEQ ID NO: 37)
V V Y T D C T E S G Q N L C L C E G S V V C G Q G
N K C T Q G S D G E K N Q C V T G E G T P K P E S
H N D G D F E E I P E E Y L Q

M 35 (SEQ ID NO: 38)
V V Y T D C T E S G Q N L C L C E G S V V C G Q G
N K C T R G S D G E K N Q C V T G E G T P K P E S
H N D G D F E E I P E E Y L Q

M 36 (SEQ ID NO: 39)
V V Y T D C T E S G Q N L C L C E G S V V C G Q G
N K C T T G S D G E K N Q C V T G E G T P K P E S
H N D G D F E E I P E E Y L Q

M 37 (SEQ ID NO: 40)
V V Y T D C T E S G Q N T C L C E G S V V C G Q G
N K C I L G S D G E K N Q C V T G E G T P K P E S
H N D G D F E E I P E E Y L Q

M 38 (SEQ ID NO: 41)
V V Y T D C T E S G Q N L C A C E G S V V C G Q G
N K C I L G S D G E K N Q C V T G E G T P K P E S
H N D G D F E E I P E E Y L Q

M 39 (SEQ ID NO: 42)
V V Y T D C T E S G Q N L C H C E G S V V C G Q G
N K C I L G S D G E K N Q C V T G E G T P K P E S
H N D G D F E E I P E E Y L Q

M 40 (SEQ ID NO: 43)
V V Y T D C T E S G Q N L C Q C E G S V V C G Q G
N K C I L G S D G E K N Q C V T G E G T P K P E S
H N D G D F E E I P E E Y L Q

M 41 (SEQ ID NO: 44)
V V Y T D C T E S G Q N L C T C E G S V V C G Q G
N K C I L G S D G E K N Q C V T G E G T P K P E S
H N D G D F E E I P E E Y L Q

M 42 (SEQ ID NO: 45)
V V Y T D C T E S G Q N L C L C E G S V A C G Q G
N K C I L G S D G E K N Q C V T G E G T P K P E S
H N D G D F E E I P E E Y L Q

M 43 (SEQ ID NO: 46)
V V Y T D C T E S G Q N L C L C E G S V G C G Q G
N K C I L G S D G E K N Q C V T G E G T P K P E S
H N D G D F E E I P E E Y L Q

M 44 (SEQ ID NO: 47)
V V Y T D C T E S G Q N L C L C E G S V H C G Q G
N K C I L G S D G E K N Q C V T G E G T P K P E S
H N D G D F E E I P E E Y L Q

M 45 (SEQ ID NO: 48)
V V Y T D C T E S G Q N L C L C E G S V K C G Q G
N K C I L G S D G E K N Q C V T G E G T P K P E S
H N D G D F E E I P E E Y L Q

TABLE A-continued

Sequences of modified (M1-M81) and wild-type hirudin (M82), and T-cell epitope containing region A within wild-type hirudin:

M 46 (SEQ ID NO: 49)
V V Y T D C T E S G Q N L C L C E G S V N C G Q G
N K C I L G S D G E K N Q C V T G E G T P K P E S
H N D G D F E E I P E E Y L Q

M 47 (SEQ ID NO: 50)
V V Y T D C T E S G Q N L C L C E G S V P C G Q G
N K C I L G S D G E K N Q C V T G E G T P K P E S
H N D G D F E E I P E E Y L Q

M 48 (SEQ ID NO: 51)
V V Y T D C T E S G Q N L C L C E G S V Q C G Q G
N K C I L G S D G E K N Q C V T G E G T P K P E S
H N D G D F E E I P E E Y L Q

M 49 (SEQ ID NO: 52)
V V Y T D C T E S G Q N L C L C E G S V R C G Q G
N K C I L G S D G E K N Q C V T G E G T P K P E S
H N D G D F E E I P E E Y L Q

M 50 (SEQ ID NO: 53)
V V Y T D C T E S G Q N L C L C E G S V V C G Q G
N K C A L G S D G E K N Q C V T G E G T P K P E S
H N D G D F E E I P E E Y L Q

M 51 (SEQ ID NO: 54)
V V Y T D C T E S G Q N L C L C E G S V V C G Q G
N K C D L G S D G E K N Q C V T G E G T P K P E S
H N D G D F E E I P E E Y L Q

M 52 (SEQ ID NO: 55)
V V Y T D C T E S G Q N L C L C E G S V V C G Q G
N K C E L G S D G E K N Q C V T G E G T P K P E S
H N D G D F E E I P E E Y L Q

M 53 (SEQ ID NO: 56)
V V Y T D C T E S G Q N L C L C E G S V V C G Q G
N K C G L G S D G E K N Q C V T G E G T P K P E S
H N D G D F E E I P E E Y L Q

M 54 (SEQ ID NO: 57)
V V Y T D C T E S G Q N L C L C E G S V V C G Q G
N K C H L G S D G E K N Q C V T G E G T P K P E S
H N D G D F E E I P E E Y L Q

M 55 (SEQ ID NO: 58)
V V Y T D C T E S G Q N L C L C E G S V V C G Q G
N K C K L G S D G E K N Q C V T G E G T P K P E S
H N D G D F E E I P E E Y L Q

M 56 (SEQ ID NO: 59)
V V Y T D C T E S G Q N L C L C E G S V V C G Q G
N K C N L G S D G E K N Q C V T G E G T P K P E S
H N D G D F E E I P E E Y L Q

M 57 (SEQ ID NO: 60)
V V Y T D C T E S G Q N L C L C E G S V V C G Q G
N K C Q L G S D G E K N Q C V T G E G T P K P E S
H N D G D F E E I P E E Y L Q

M 58 (SEQ ID NO: 61)
V V Y T D C T E S G Q N L C L C E G S V V C G Q G
N K C R L G S D G E K N Q C V T G E G T P K P E S
H N D G D F E E I P E E Y L Q

M 59 (SEQ ID NO: 62)
V V Y T D C T E S G Q N L C L C E G S V V C G Q G
N K C S L G S D G E K N Q C V T G E G T P K P E S
H N D G D F E E I P E E Y L Q

M 60 (SEQ ID NO: 63)
V V Y T D C T E S G Q N L C L C E G S V V C G Q G
N K C T L G S D G E K N Q C V T G E G T P K P E S
H N D G D F E E I P E E Y L Q

M 61 (SEQ ID NO: 64)
V V Y T D C T E S G Q N L C L C E G S V V C G Q G
N K C I A G S D G E K N Q C V T G E G T P K P E S
H N D G D F E E I P E E Y L Q

M 62 (SEQ ID NO: 65)
V V Y T D C T E S G Q N L C L C E G S V V C G Q G
N K C I D G S D G E K N Q C V T G E G T P K P E S
H N D G D F E E I P E E Y L Q

M63 (SEQ ID NO: 66)
V V Y T D C T E S G Q N L C L C E G S V V C G Q G
N K C I E G S D G E K N Q C V T G E G T P K P E S
H N D G D F E E I P E E Y L Q

M 64 (SEQ ID NO: 67)
V V Y T D C T E S G Q N L C L C E G S V V C G Q G
N K C I G G S D G E K N Q C V T G E G T P K P E S
H N D G D F E E I P E E Y L Q

M 65 (SEQ ID NO: 68)
V V Y T D C T E S G Q N L C L C E G S V V C G Q G
N K C I H G S D G E K N Q C V T G E G T P K P E S
H N D G D F E E I P E E Y L Q

M 66 (SEQ ID NO: 69)
V V Y T D C T E S G Q N L C L C E G S V V C G Q G
N K C I K G S D G E K N Q C V T G E G T P K P E S
H N D G D F E E I P E E Y L Q

M 67 (SEQ ID NO: 70)
V V Y T D C T E S G Q N L C L C E G S V V C G Q G
N K C I N G S D G E K N Q C V T G E G T P K P E S
H N D G D F E E I P E E Y L Q

M 68 (SEQ ID NO: 71)
V V Y T D C T E S G Q N L C L C E G S V V C G Q G
N K C I P G S D G E K N Q C V T G E G T P K P E S
H N D G D F E E I P E E Y L Q

M 69 (SEQ ID NO: 72)
V V Y T D C T E S G Q N L C L C E G S V V C G Q G
N K C I Q G S D G E K N Q C V T G E G T P K P E S
H N D G D F E E I P E E Y L Q

M 70 (SEQ ID NO: 73)
V V Y T D C T E S G Q N L C L C E G S V V C G Q G
N K C I R G S D G E K N Q C V T G E G T P K P E S
H N D G D F E E I P E E Y L Q

M 71 (SEQ ID NO: 74)
V V Y T D C T E S G Q N L C L C E G S V V C G Q G
N K C I S G S D G E K N Q C V T G E G T P K P E S
H N D G D F E E I P E E Y L Q

M 72 (SEQ ID NO: 75)
V V Y T D C T E S G Q N L C L C E G S V V C G Q G
N K C I T G S D G E K N Q C V T G E G T P K P E S
H N D G D F E E I P E E Y L Q

M 73 (SEQ ID NO: 76)
V V Y T D C T E S G Q N L C L C E G S V V C G Q G
N K C I L G S D G E K N Q C A T G E G T P K P E S
H N D G D F E E I P E E Y L Q

M 74 (SEQ ID NO: 77)
V V Y T D C T E S G Q N L C L C E G S V V C G Q G
N K C I L G S D G E K N Q C T T G E G T P K P E S
H N D G D F E E I P E E Y L Q

M 75 (SEQ ID NO: 78)
V V Y T D C T E S G Q N L C L C E G S V V C G Q G
N K C I L G S D G E K N Q C V T G E G T P T P E S
H N D G D F E E I P E E Y L Q

TABLE A-continued

Sequences of modified (M1-M81) and wild-type hirudin (M82), and T-cell epitope containing region A within wild-type hirudin:

M 76 (SEQ ID NO: 79)
V V Y T D C T E S G Q N L C L C E G S V V C G Q G
N K C I L G S D G E K N Q C V T G E G T P K A E S
H N D G D F E E I P E E Y L Q

M 77 (SEQ ID NO: 80)
V V Y T D C T E S G Q N L C L C E G S V V C G Q G
N K C I L G S D G E K N Q C V T G E G T P K T E S
H N D G D F E E I P E E Y L Q

M 78 (SEQ ID NO: 81)
V V Y T D C T E S G Q N L C L C E G S V V C G Q G
N K C I L G S D G E K N Q C V T G E G T P K P E S
H N E G D F E E I P E E Y L Q

M 79 (SEQ ID NO: 82)
V V Y T D C T E S G Q N L C L C E G S V V C G Q G
N K C I L G S D G E K N Q C V T G E G T P K P E S
H N N G D F E E I P E E Y L Q

M 80 (SEQ ID NO: 83)
V V Y T D C T E S G Q N L C L C E G S V V C G Q G
N K C I L G S D G E K N Q C V T G E G T P K P E S
H N R G D F E E I P E E Y L Q

M 81 (SEQ ID NO: 84)
V V Y T D C T E S G Q N L C L C E G S V V C G Q G
N K C I L G S D G E K N Q C V T G E G T P K P E S
H N D G D H E E I P E E Y L Q

M 82 (SEQ ID NO: 3)
V V Y T D C T E S G Q N L C L C E G S V V C G Q G
N K C I L G S D G E K N Q C V T G E G T P K P E S
H N D G D F E E I P E E Y L Q (A) (SEQ ID NO: 1):
C I L G S D G E K N Q C V T G E G T P K P E S H N
D G D F E

DESCRIPTION OF THE FIGURES

FIG. 1:

Figure 2:
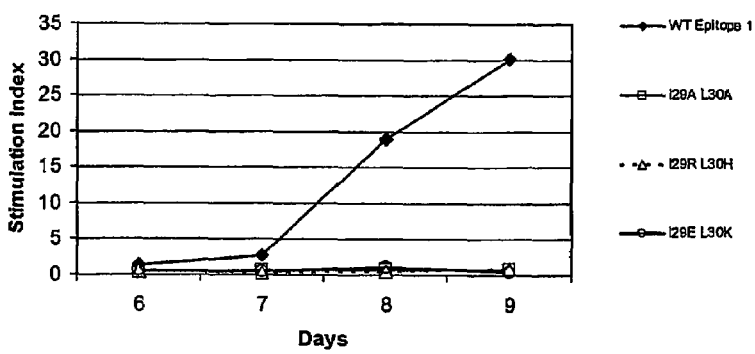
Figure 2:
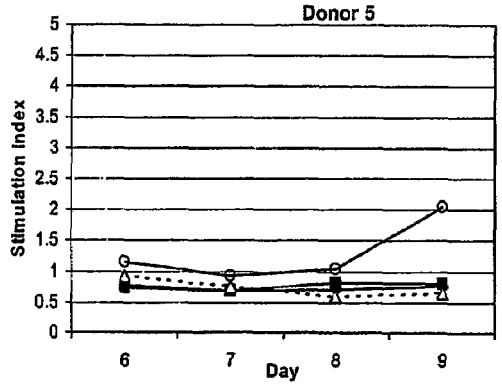
Figure 2:
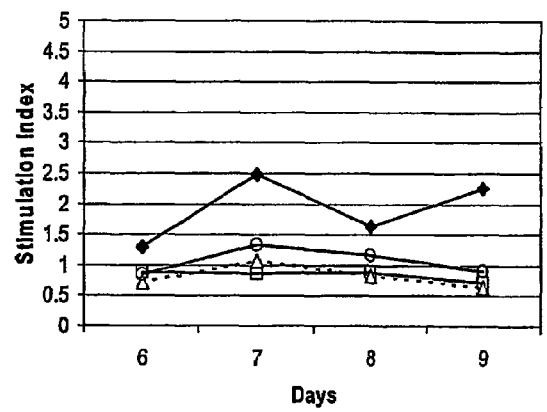
Figure 2:
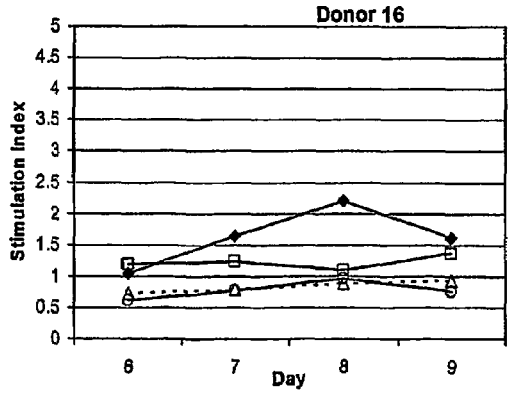
Figure 2:
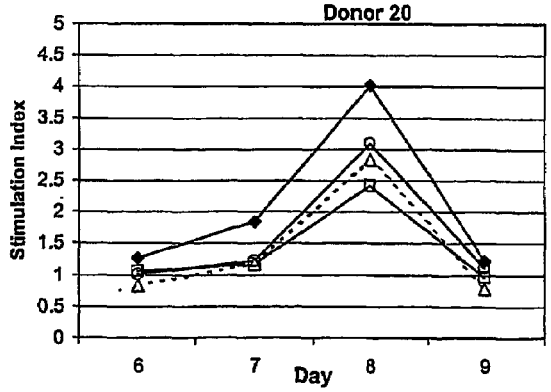
Figure 4:
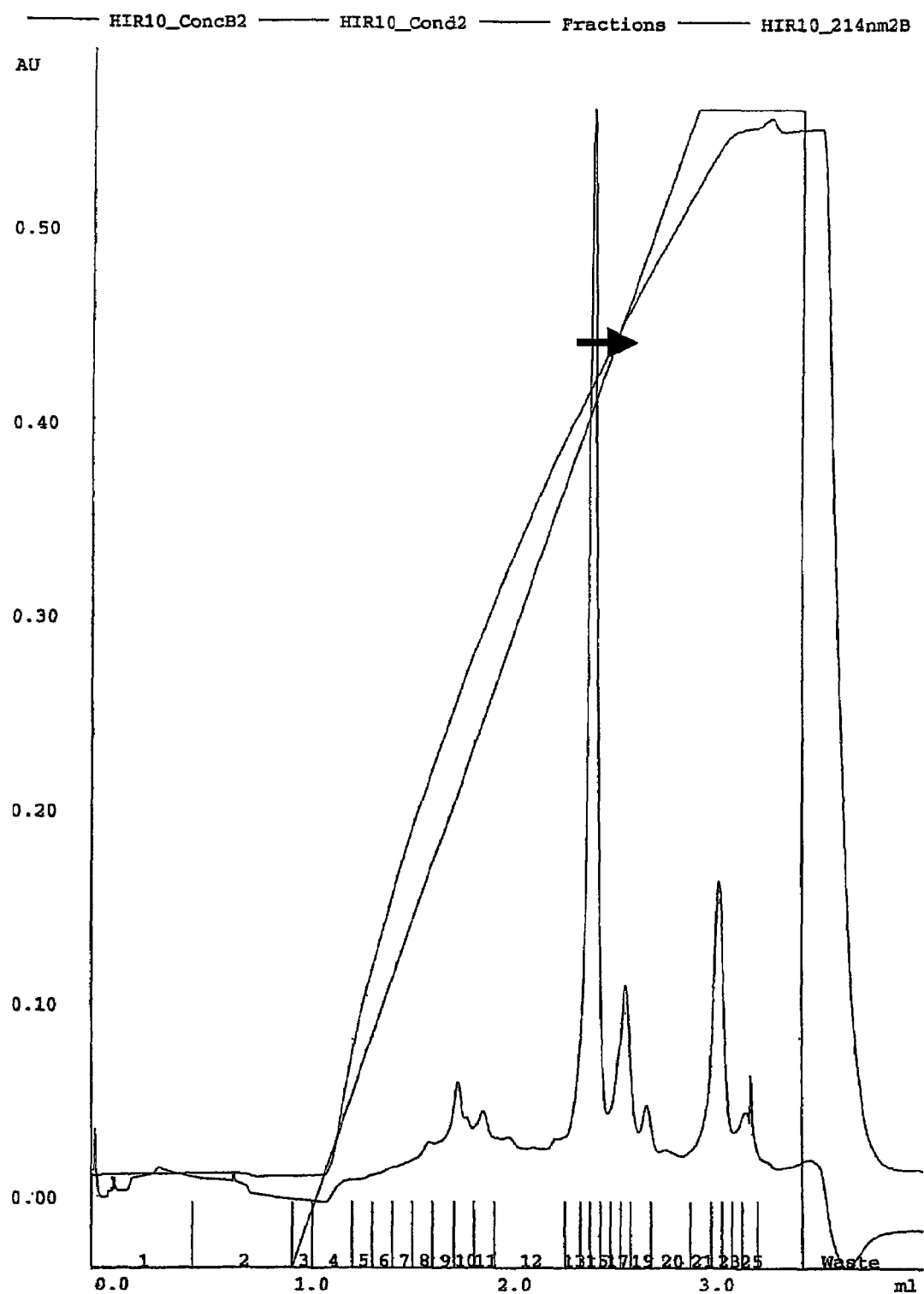
Figure 5:
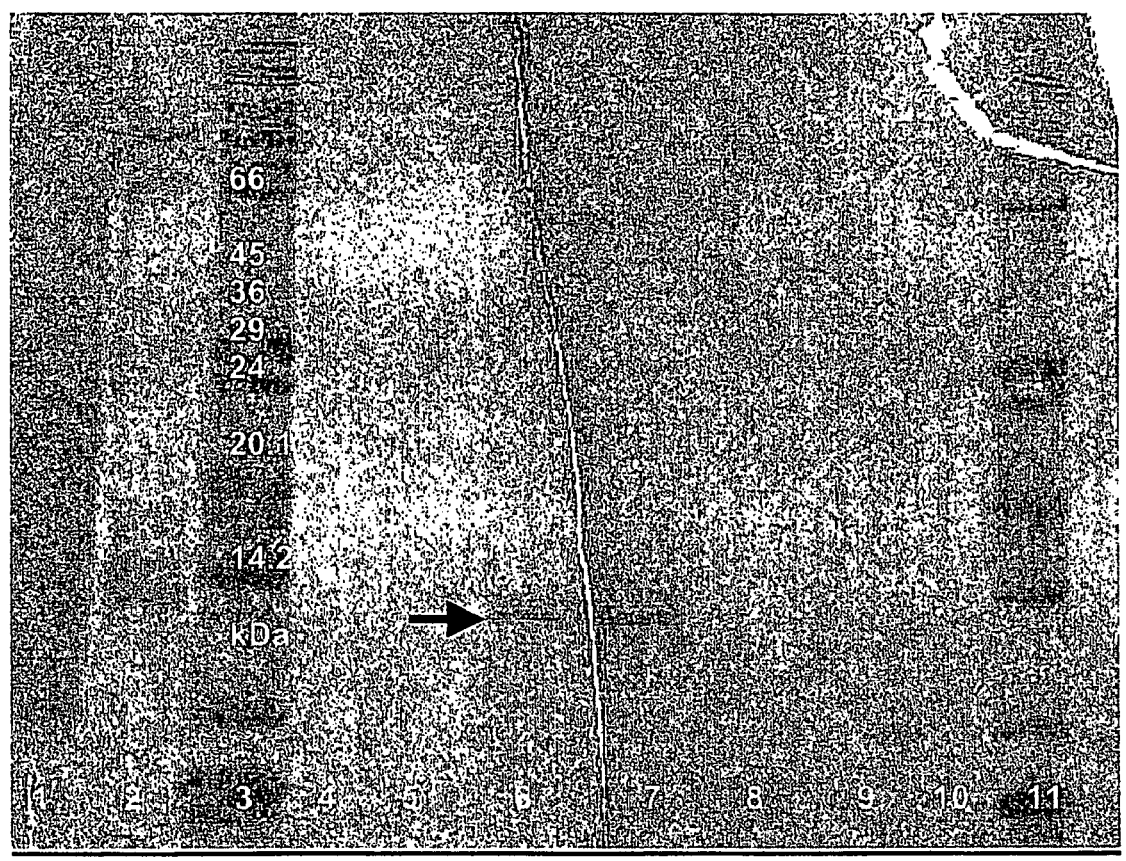
Figure 6:
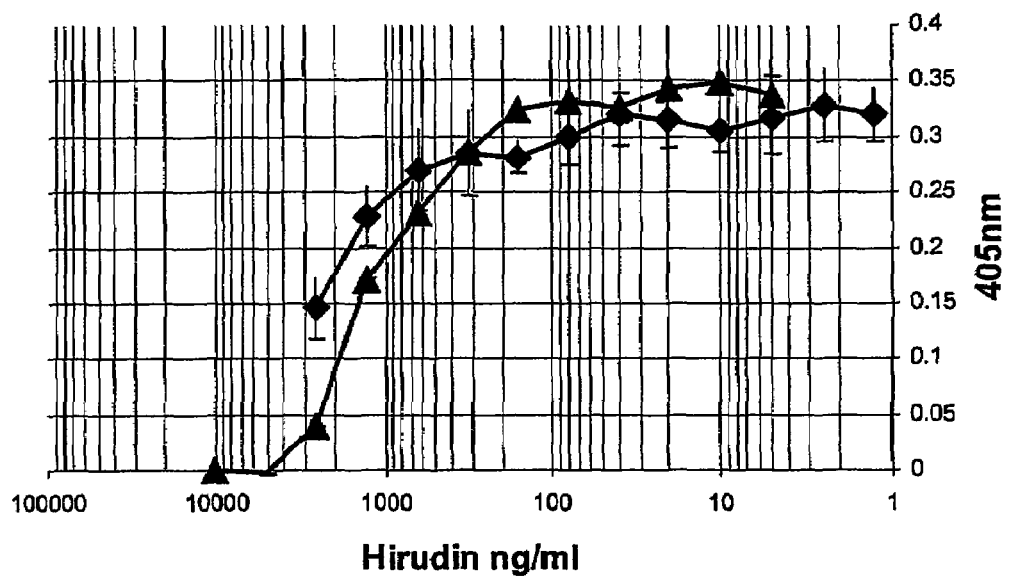
Figure 6:
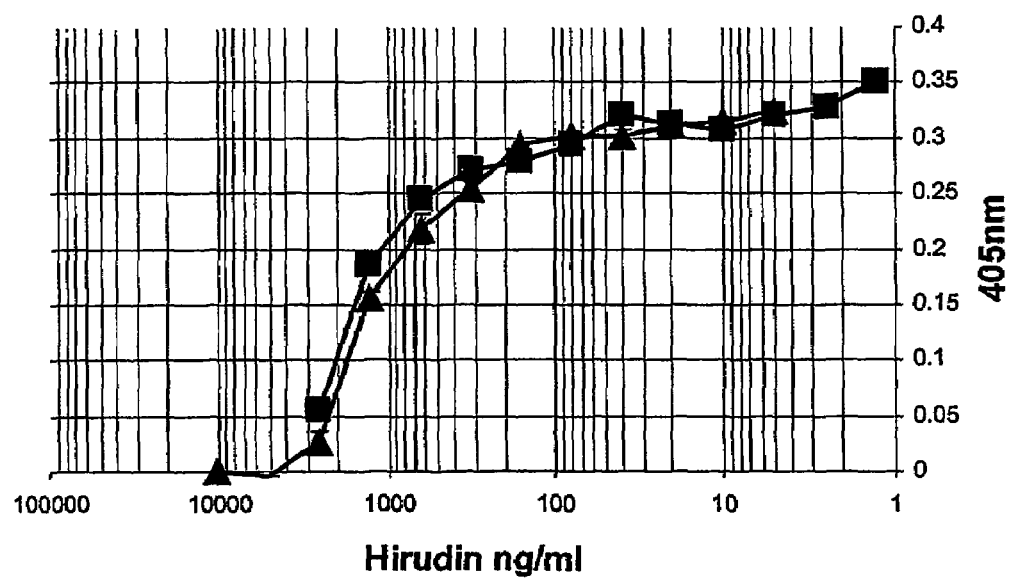

The mature sequence of [Val$^1$ Val$^2$]-hirudin (SEQ ID NO: 3) with regions of immunogenicity highlighted in bold. The most preferred modifications are to residues 29 and 30 (underlined). The preferred alternative substitutions are indicated above the sequence.

FIG. 2:

Immunogenicity of [Val$^1$ Val$^2$]-hirudin variant peptides. Two cohorts of 20 healthy donors were used to test the immunogenicity of wild type region 1 and modified region 1 peptides. Proliferation of PBMC was assessed by tritiated thymidine incorporation on days 6, 7, 8 and 9 post-stimulation and stimulation indexes were calculated and plotted.

FIG. 3:

Frequency of observed responses with an SI>2 at any time point from cohorts of 20 healthy donors to either wild type [Val$^1$ Val$^2$]-hirudin region 1 and modified R1 peptides.

FIG. 4:

Purification of [Val$^1$ Val$^2$]-hirudin from transfected HEK.293 cell supernatants. Elution of pooled fractions from pH 7.0 elution on Mono Q column at pH 5.5. Main peak containing hirudin is marked with an arrow.

FIG. 5:

Silver stained SDS-PAGE gel of fractions from elution of Mono Q column at pH 5.5. Lane 1=diluted supernatant loaded onto Mono Q column at pH 7.0; Lane 2=Concentrated factions from elution of Mono Q column at pH 7.0; Lane 3=Protein Standards; Lane 4=Fraction 1 pH 5.5 elution; Lane 5=Fraction 10 pH 5.5 elution; Lane 6=Fraction 14 pH 5.5 elution; Lane 7=Fraction 15 pH 5.5 elution; Lane 8=Fraction 17 pH 5.5 elution; Lane 9=Fraction 19 pH 5.5 elution; Lane 10=Fraction 22 pH 5.5 elution; Lane 11=Protein Standards. Bands corresponding to hirudin in lanes 6 and 7 are marked with an arrow.

FIG. 6:

Thrombin inhibitory activity of the hirudin variants: I29A L30A and I29R L30H (M 1 and M 2 respectively). Cell-culture supernatants from I29A L30A(♦), I29R L30H (■) and WT hirudin (▲) from transfected HEK.293 cells, were compared in the chromogenic thrombin cleavage assay. The amount of hirudin variants in tissue culture supernatants were quantified by ELISA, and the thrombin inhibition activity was titrated in 2 fold serial dilutions.

EXPERIMENTAL EXAMPLES

Example 1

Construction of Hirudin Muteins

The cDNA for Hirudin was cloned from a cDNA library obtained by RT-PCR from mRNA extracted from the head of the medicinal leech, Hirudo medicinalis (Biopharm Ltd., Hendy, UK) using a Qiagen total RNA extraction kit (Qiagen, Crawley, UK) according to the manufacturer's instructions. This sequence was mutated to that of [Val$^1$ Val$^2$]-hirudin, by site directed mutagenesis PCR [Higuchi et al (1988) Nucleic Acids Res. 16: 7351].

For protein expression, the native 20 amino acid secretion signal, (MFSLKLFVVFLAVCICVSQA, SEQ ID NO: 85, of a hirudin variant from the Asian buffalo leech (*Hirudinaria manillensis*) was added by PCR and this construct was then sub-cloned into the expression vector pREP4 (Invitrogen, Paisley, UK). Later a modified secretion signal (MVSLKLFVVFLAVCICVSQA; SEQ ID NO: 86) was used in order to create a more efficient Kozak consensus sequence for protein expression in mammalian cell lines [Kozak, M. (1987) *Nucleic Acids Research;* 15: 8125-8148; Kozak M. (1991) *Journal of Cell Biology;* 115: 887-903; Kozak, M. (1990) *Proc. Natl. Acad. Sci. (USA);* 87: 8301-8305], where the mutation of F$^2$ (TTC) to a V (GTC) placed a guanosine residue at position +4 in the consensus sequence.

A total of 107 different hirudin muteins were constructed using PCR mutagenesis and the WT gene as a template. DNA sequencing was conducted on all constructs. This was diligently performed to confirm introduction of desired substitutions and establish that no extraneous (undesired) substitutions had been introduced for example by PCR error.

Example 2

Expression and Purification of Hirudin Proteins

Expression plasmids containing hirudin mutein genes were tranfected into the human embryonic kidney cell line HEK.293. Transfection was conducted using lipofectamine transfection reagent and cells were cultured in DMEM media free of phenol red (Invitrogen, Paisley, UK). Hirudin was purified from the culture media. Briefly, tissue culture supernatant was diluted 1:1 with Mono Q buffer A (20 mM Bis-Tris-Propane pH 7.0). This was then filtered through a 0.22 μM membrane and applied to a Mono Q (HR5/5) column and protein was eluted using a 0-100% NaCl gradient in buffer A. Fractions were then tested for the presence of hirudin by ELISA.

Hirudin enriched fractions were pooled and concentrated using a Centricon centrifugal concentrator fitted with a YM3 membrane (3 kDa MW cut off). The pooled and concentrated fractions were buffer exchanged (G25 column) into buffer B (20 mM Piperazine pH 5.5) and, applied to a Mono Q column equilibrated with buffer B. Protein was eluted with a gradient from 0-100% 0.5M NaCl in buffer B and was monitored at 214 nm. Peak fractions were analysed on a 4-12% Bis-Tris SDS-PAGE gel (Invitrogen, Paisley, UK) using MES buffer. The gel was then silver stained to check the purity of the fractions.

Example 3

Detection and Quantitation of Hirudin Variants

Expressed hirudin was detected and quantitated using an ELISA with a matched pair of anti-hirudin antibodies [Koch C, et al (1993) *Analytical Biochemistry;* 214: 301-312]. Hirudin purified from *Hirudo medicinalis* saliva (Roche, Lewes, UK) was used as a standard in order to quantify expression. Briefly, a 96 well plate was coated with 100 μl of mouse anti-hirudin N-terminal epitope (Antibody shop, Copenhagen, Denmark) at 10 μg/ml in PBS, overnight at 4° C. The plate was washed once with PBS/0.05% Tween, 200 μl per well, then blocked with 200 μl per well of PBS/2% BSA for one hour at room temperature. The plate was then washed 5× with PBS/0.05% Tween, 200 μl per well, then blotted onto pad of paper tissues to remove excess liquid. A hirudin standard curve starting with 1280 ng/ml was set up using doubling dilutions vertically down the plate. Hirudin variant samples were added in triplicate to a final volume of 100 μl in PBS at dilutions of 1:50 and 1:100. The plate was incubated for 1 hr at room temperature then washed 5× as described above. 100 μl of biotinylated mouse anti-hirudin C-terminal epitope (Antibody Shop, Copenhagen, Denmark) was added at a 1:1000 dilution in PBS/2% BSA to each well and the plate incubated for 1 hr at room temperature. The plate was washed 5× as described above. 100 μl of streptavidin peroxidase (Sigma, Poole, UK) 1:1000 dilution in PBS/2% BSA was added and the plate was incubated for 1 hr at room temperature. The plate was washed as described above and 100 μl of o-phenylenediamine dihydrochloride substrate (Sigma, Poole, UK) was added to each well and the plate incubated at room temperature for 5 minutes. The reaction was quenched by adding 50 μl of 1M $H_2SO_4$ to each well and the absorbance measured at 492 nm.

Example 4

Functional Activity of Hirudin Muteins

The functional activity of the modified hirudin proteins was assessed using a chromogenic thrombin inhibition assay. In this assay, a fixed amount of thrombin is incubated with a range of hirudin concentrations at 37° C. The chromogenic substrate H-D-Phe-Pep-Arg-pNA is then added and any residual free thrombin present will cleave the substrate to form H-D-Phe-Pep-Arg-OH and pNA that can then be detected spectrophotometrically at 405 nm Briefly, 2 ml of $dH_2O$ was added to the thrombin vial and the H-D-Phe-Pep-Arg-pNA substrate vial from a Diagnostica Stago Stachrom HCII assay kit (Axis Shield Diagnostics, Dundee, UK) and they were both warmed in an incubator to 37° C. Hirudin assay buffer (175 mM NaCl, 7.5 mM $Na_2$ EDTA, 50 mM Tris-HCl pH 8.4) was warmed to 37° C. then used to dilute the test hirudin protein variants, hirudin wild type and hirudin control (Roche, Lewes, UK) proteins.

Aliquots of 40 μl of warm hirudin assay buffer were pipetted into wells A-H 2-12 of a clear 96 well flat bottom plate, then 40 μl aliquots of hirudin samples were placed into the wells in columns 1 and 2. Using a multichannel mix by pipetting up and down the contents of wells in column 2 and prepare a serial doubling dilution of the samples were made horizontally across the plate by removing 40 μl from column 2 and adding to column 3 etc.

The plate was warmed to 37° C. for 5 minutes followed by addition of 40 μl thrombin and incubated for 120 seconds at 37° C. with shaking. 40 μl H-D-Phe-Pep-Arg-pNA substrate was added, the plate and incubated for 90 seconds at 37° C. with shaking. 40 μl acetic acid was added to quench reaction and the plate was read spectrophotometrically at 405 nm. Absorbance at 405 nm vs hirudin concentration was plotted using Sigma plot (Sigma Poole, UK) and $IC_{50}$ values calculated by fitting a sigmoidal equation.

A total of 81 different hirudin variants demonstrated positive activity in the chromogenic thrombin inhibition assay. Others either failed to express or showed no acceptable degree of activity. Positive activity was taken to be a relative activity value of less than 10. Relative activity was determined by dividing the $ED_{50}$ value derived for the protein of interest by the $ED_{50}$ value derived for the control (WT) protein.

Of these active proteins, 45 were muteins comprising a single amino acid substitution; 27 comprised two amino acid substitutions and 9 comprised three amino acid substitutions. The sequence of each of these active hirudin muteins is provided in M 1-81. The relative activities of each functioning mutein are provided in Table 2 in which the heading labeled "Substitution" refers to substitutions in SEQ ID NO: 3.

A number of muteins show improved activity relative to the WT molecule. All active muteins are embodiments of the invention.

TABLE 2

Activity of hirudin variants

| Substitution | Relative Activity* | Substitution | Relative Activity* |
|---|---|---|---|
| L13T | 0.60 | D53E | 1.0 |
| L15A | 0.90 | D53N | 1.0 |
| L15H | 0.65 | D53R | 1.0 |
| L15Q | 0.34 | F56H | 0.80 |
| L15T | 0.40 | I29A L3QA | 1.40 |
| V21A | 0.93 | I29A L30K | 1.45 |
| V21G | 1.0 | I29A L30Q | 1.60 |
| V21H | 0.74 | I29A L30R | 2.70 |
| V21K | 0.90 | I29A L30T | 1.21 |
| V21N | 0.83 | I29D L30A | 1.60 |
| V21P | 1.0 | I29D L30Q | 2.0 |
| V21Q | 0.83 | I29D L30R | 2.5 |
| V21R | 0.77 | I29E L30K | 1.10 |
| I29A | 1.0 | I29E L30Q | 1.52 |
| I29D | 1.0 | I29E L30R | 1.21 |
| I29E | 1.0 | I29E I30T | 1.80 |
| I29G | 1.8 | I29R L30H | 1.2 |
| I29H | 1.0 | I29R L30K | 0.93 |
| I29K | 1.0 | I29R L30Q | 1.0 |
| I29N | 1.0 | I29R L30R | 1.0 |
| I29Q | 1.0 | I29R L30T | 1.0 |
| I29R | 1.0 | I29S L30A | 1.34 |
| I29S | 1.0 | I29S L30K | 1.50 |
| I29T | 1.0 | I29S L30Q | 2.0 |
| L30A | 1.0 | I29S L30R | 2.5 |
| L30D | 2.0 | I29S L30T | 1.10 |

TABLE 2-continued

Activity of hirudin variants

| Substitution | Relative Activity* | Substitution | Relative Activity* |
|---|---|---|---|
| L30E | 3.33 | I29T L30A | 1.67 |
| L30G | 2.20 | I29T L30K | 1.60 |
| L30H | 1.0 | I29T L30Q | 2.4 |
| L30K | 1.0 | I29T L30R | 2.30 |
| L30N | 1.54 | I29T L30T | 1.80 |
| L30P | 1.83 | I29R L30K | 0.20 |
| L30Q | 1.0 | I29R L30K | 0.36 |
| L30R | 1.0 | I29R L30K | 0.70 |
| L30S | 1.83 | I29E L30K | 1.0 |
| L30T | 1.0 | I29E L30K | 1.0 |
| V40A | 1.0 | I29E L30K | 0.55 |
| V40T | 1.0 | I29E L30K | 1.0 |
| K47T | 2.2 | I29R L30K | 0.70 |
| P48A | 1.0 | I29R L30K | 0.80 |
| P48T | 1.0 | | |

*Ratio of variant IC$_{50}$/WT IC$_{50}$

Example 5

Identification of T-Cell Epitopes in Hirudin

All blood samples used in this study were obtained with approval of the Addenbrooke's Hospital Local Research Ethics Committee. T-cell epitope mapping was performed using human PBMCs isolated from blood obtained from the National Blood Transfusion Service (Addenbrooke's Hospital, Cambridge, UK). PBMCs from 25 healthy donors were isolated by Ficoll density centrifugation and stored under liquid nitrogen. Each donor was tissue-typed using an Allset™ PCR based tissue-typing kit (Dynal) and T cell assays were performed by selecting donors according to individual MHC haplotypes. 15 mer peptides staggered by three amino acids and spanning the human hirudin sequence were purchased from Pepscan Systems BV (NL). Using this scheme, total of 19 peptides were required to scan the hirudin protein. The sequence and peptide number of these peptides are provided in Table 3.

TABLE 3

Peptides used to map immunogenic epitopes within hirudin

| Peptide No | SEQ ID NO: | Peptide sequence |
|---|---|---|
| 1 | 87 | VVYTDCTESGQNLCL |
| 2 | 88 | LTYTDCTESGQNLCL |
| 3 | 89 | TDCTESGQNLCLCEG |
| 4 | 90 | TESGQNLCLCEGSNV |
| 5 | 91 | GQNLCLCEGSNVCGQ |
| 6 | 92 | LCLCEGSNVCGQGNK |
| 7 | 93 | CEGSNVCGQGNKCIL |
| 8 | 94 | SNVCGQGNKCILGSD |
| 9 | 95 | CGQGNKCILGSDGEK |
| 10 | 96 | GNKCILGSDGEKNQC |
| 11 | 97 | CILGSDGEKNQCVTG |
| 12 | 98 | GSDGEKNQCVTGEGT |
| 13 | 99 | GEKNQCVTGEGTPKP |
| 14 | 100 | NQCVTGEGTPKPESH |
| 15 | 101 | VTGEGTPKPESHNDG |
| 16 | 102 | EGTPKPESHNDGDFE |
| 17 | 103 | PKPESHNDGDFEEIP |
| 18 | 104 | ESHNDGDFEEIPEEY |
| 19 | 105 | NDGDFEEIPEEYYLQ |

For each donor sample, PBMCs were thawed and resuspended in AIM-V (Invitrogen) containing 100 units/ml penicillin, 100 µg/ml streptomycin and 1 mM glutamine. Triplicate cultures of 2×10$^5$ PBMC/well of flat-bottomed 96 well plate were incubated with peptides at a final concentration of 1 µM and 10 µM. Cells were incubated for 7 days before pulsing with 1 µCi/well tritiated thymidine for 18 hours. Cultures were harvested onto glass fibre filter mats using a Tomtec Mach III plate harvester and cpm values determined by scintillation counting using Wallac Microbeta TriLux plate reader.

Each donor was also tested for their ability to respond to two positive control peptides influenza haemagglutinin A amino acids 307-319 [Krieger J I, et al (1991) *Journal of Immunology;* 146: 2331-2340] and chlamydia HSP60 amino acids 125-140 [Cerrone M C, et al (1991) *Infection and Immunity;* 59: 79-90]. Keyhole limpet haemocyanin, a well documented potent T cell antigen was also used as a control.

Donors that responded to peptides with an SI>2 were analyzed further by plotting the frequency of donor responses to each peptide. Prominent regions of immunogencity were determined by peptides that induced responses in 10% of donors; however, borderline responses where individual SI values >1.95 were achieved and if two adjacent peptides induced responses in 5% of donors.

In the initial analysis using 25 donor samples, peptides located within two separate regions were able to induce T cell proliferation R1 was located at peptide 10 where donor response was 8% and R2 located at peptide 15 where the donor response was also 8%. Subsequent analysis using further 30 donor samples failed to maintain the 8% donor response rate for peptide 15 within R2 epitope region (see example 6). The final response rate across a total of 55 donor samples for peptide 15 was 4% (2/55) and R2 was not considered a significant epitope. FIG. 1 shows the mature sequence of [Val$^1$ Val$^2$]-hirudin with regions of immunogenicity highlighted in bold.

Example 6

Analysis of Immunogenic Regions by Time-Course T-Cell Assays

Bulk cultures of 2-4×10⁶ PBMC/well were established from 20 healthy donor samples in 24 well plates. Cells were incubated for 6 to 9 days with WT and variant peptides spanning the immunogenic regions (see Table 4). T cell proliferation was assessed by triated thymidine incorporation on days 6, 7, 8 and 9. Proliferation was assessed at each time point, by gently resuspending the bulk cultures and removing samples of PBMC, that were then incubated in triplicate wells of U-bottomed 96 well plate with 1 µCi/well tritiated thymidine for 18 hours as described above.

Figure 3:
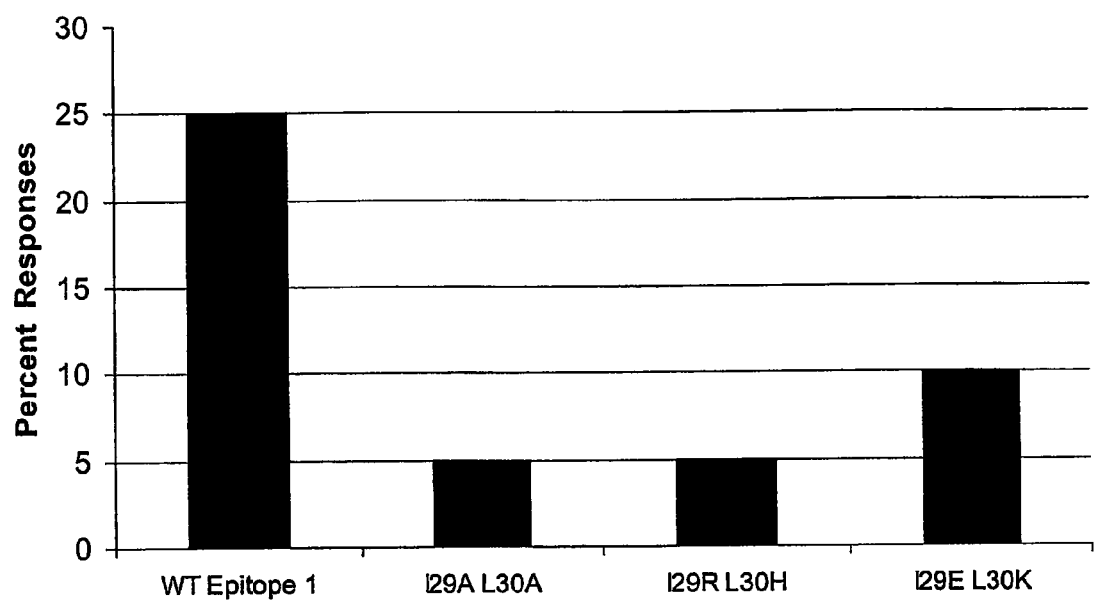

The time course assay was used to test variant peptides containing substitutions over WT. Substitutions were made at key locations where there was expectation that the substitution would prevent binding to MHC class II and therefore, subsequent T cell proliferation in the assay. FIG. 2 and FIG. 3 respectively show exemplary donor responses over the time course and overall response frequencies. Table 4 shows the sequences of the peptides tested and also the overall response frequencies to each peptide.

The frequency of response is significantly reduced for all substitutions tested. The most effective substitutions are I29A L30A (M 1) and I29R L30H (M 2).

TABLE 4

Sequences of peptides used in time-course assays

| Wild Type Sequence | % donor response in time course | Modified Sequences | % donor response in time course |
|---|---|---|---|
| CILGSDGEKNQCVTG SEQ ID NO: 97 | 25 | CAAGSDGEKNQCVTG SEQ ID NO: 106 | 5 |
| | | CEKGSDGEKNQCVTG SEQ ID NO: 107 | 10 |
| | | CRHGSDGEKNQCVTG SEQ ID NO: 108 | 5 |

Example 7

Functional Activity of Most Preferred Hirudin Muteins

The thrombin inhibitory activity of the most preferred molecules of the invention was tested. Results are shown in Table 5. Cell-culture supernatants from variants and WT hirudin from transfected HEK.293 cells, were compared in the chromogenic thrombin cleavage assay. The amount of hirudin variants in tissue culture supernatants were quantified by ELISA, and the thrombin inhibition activity was titrated in 2 fold serial dilutions.

The most preferred molecules of the invention demonstrate functional activity within 60% of the WT molecule.

TABLE 5

Functional activity of most preferred hirudin muteins

| Hirudin variant | Relative activity ($ED_{50}$ variant/$ED_{50}$ WT hirudin) |
|---|---|
| I29A L30A (M 1) | 1.4 |
| I29R L30H (M 2) | 1.2 |

---

The invention claimed is:

1. An isolated peptide consisting of the amino acid residue sequence CILGSDGEKNQCVTGEGTPKPESHNDGDFE (SEQ ID NO: 1).

2. A pharmaceutical composition comprising the peptide of claim 1, optionally together with a pharmaceutically acceptable carrier, diluent or excipient.

* * * * *

SEQUENCE LISTING

<160> NUMBER OF SEQ ID NOS: 108

<210> SEQ ID NO 1
<211> LENGTH: 31
<212> TYPE: PRT
<213> ORGANISM: hirudo medicinalis

<400> SEQUENCE: 1

Ala Cys Ile Leu Gly Ser Asp Gly Glu Lys Asn Gln Cys Val Thr Gly
 1               5                  10                  15

Glu Gly Thr Pro Lys Pro Glu Ser His Asn Asp Gly Asp Phe Glu
             20                  25                  30

<210> SEQ ID NO 2
<211> LENGTH: 65

```
<212> TYPE: PRT
<213> ORGANISM: Artificial Sequence
<220> FEATURE:
<223> OTHER INFORMATION: modified hirudin
<220> FEATURE:
<221> NAME/KEY: VARIANT
<222> LOCATION: 13, 15, 21, 29
<223> OTHER INFORMATION: X=T, L;
      X=T,A,H,Q,T,L;
      X=A,G,H,K,N,P,Q,R,V;
      X=A,D,E,G,H,K,N,Q,R,S,T,I;
<220> FEATURE:
<221> NAME/KEY: VARIANT
<222> LOCATION: 30, 40, 47, 48
<223> OTHER INFORMATION: X=A,D,E,G,H,K,N,P,Q,R,S,T,L;
      X=A,T,V;
      X=T,K;
      X=A,T,P
<220> FEATURE:
<221> NAME/KEY: VARIANT
<222> LOCATION: 53, 56
<223> OTHER INFORMATION: X=E,N,R,D;
      X=H,F

<400> SEQUENCE: 2
```

Val Val Tyr Thr Asp Cys Thr Glu Ser Gly Gln Asn Xaa Cys Xaa Cys
 1               5                  10                  15

Glu Gly Ser Val Xaa Cys Gly Gln Gly Asn Lys Cys Xaa Xaa Gly Ser
            20                  25                  30

Asp Gly Glu Lys Asn Gln Cys Xaa Thr Gly Glu Gly Thr Pro Xaa Xaa
        35                  40                  45

Glu Ser His Asn Xaa Gly Asp Xaa Glu Glu Ile Pro Glu Glu Tyr Leu
    50                  55                  60

Gln
65

```
<210> SEQ ID NO 3
<211> LENGTH: 65
<212> TYPE: PRT
<213> ORGANISM: hirudo medicinalis

<400> SEQUENCE: 3
```

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

```
<210> SEQ ID NO 4
<211> LENGTH: 65
<212> TYPE: PRT
<213> ORGANISM: Artificial Sequence
<220> FEATURE:
<223> OTHER INFORMATION: modified hirudin

<400> SEQUENCE: 4
```

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ala Ala Gly Ser
            20                  25                  30

```
Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 5
<211> LENGTH: 65
<212> TYPE: PRT
<213> ORGANISM: Artificial Sequence
<220> FEATURE:
<223> OTHER INFORMATION: modified hirudin

<400> SEQUENCE: 5

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Arg His Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 6
<211> LENGTH: 65
<212> TYPE: PRT
<213> ORGANISM: Artificial Sequence
<220> FEATURE:
<223> OTHER INFORMATION: modified hirudin

<400> SEQUENCE: 6

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Glu Lys Gly Ser
            20                  25                  30

Asp Gly Glu Lys Asn Gln Cys Ala Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 7
<211> LENGTH: 65
<212> TYPE: PRT
<213> ORGANISM: Artificial Sequence
<220> FEATURE:
<223> OTHER INFORMATION: modified hirudin

<400> SEQUENCE: 7

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Glu Lys Gly Ser
            20                  25                  30

Asp Gly Glu Lys Asn Gln Cys Thr Thr Gly Glu Gly Thr Pro Lys Pro
        35                  40                  45
```

Glu Ser His Asn Asp Gly Asp Phe Glu Glu Ile Pro Glu Glu Tyr Leu
    50                  55                  60

Gln
65

<210> SEQ ID NO 8
<211> LENGTH: 65
<212> TYPE: PRT
<213> ORGANISM: Artificial Sequence
<220> FEATURE:
<223> OTHER INFORMATION: modified hirudin

<400> SEQUENCE: 8

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Glu Lys Gly Ser
                20                  25                  30

Asp Gly Glu Lys Asn Gln Cys Val Thr Gly Glu Gly Thr Pro Lys Pro
            35                  40                  45

Glu Ser His Asn Glu Gly Asp Phe Glu Glu Ile Pro Glu Glu Tyr Leu
    50                  55                  60

Gln
65

<210> SEQ ID NO 9
<211> LENGTH: 65
<212> TYPE: PRT
<213> ORGANISM: Artificial Sequence
<220> FEATURE:
<223> OTHER INFORMATION: modified hirudin

<400> SEQUENCE: 9

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Glu Lys Gly Ser
                20                  25                  30

Asp Gly Glu Lys Asn Gln Cys Val Thr Gly Glu Gly Thr Pro Lys Pro
            35                  40                  45

Glu Ser His Asn Asn Gly Asp Phe Glu Glu Ile Pro Glu Glu Tyr Leu
    50                  55                  60

Gln
65

<210> SEQ ID NO 10
<211> LENGTH: 65
<212> TYPE: PRT
<213> ORGANISM: Artificial Sequence
<220> FEATURE:
<223> OTHER INFORMATION: modified hirudin

<400> SEQUENCE: 10

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Arg Lys Gly Ser
                20                  25                  30

Asp Gly Glu Lys Asn Gln Cys Ala Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln

<210> SEQ ID NO 11
<211> LENGTH: 65
<212> TYPE: PRT
<213> ORGANISM: Artificial Sequence
<220> FEATURE:
<223> OTHER INFORMATION: modified hirudin

<400> SEQUENCE: 11

```
Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Arg Lys Gly Ser
             20                  25                  30

Asp Gly Glu Lys Asn Gln Cys Thr Thr Gly Gly Thr Pro Lys Pro
         35                  40                  45

Glu Ser His Asn Asp Gly Asp Phe Glu Glu Ile Pro Glu Glu Tyr Leu
     50                  55                  60

Gln
65
```

<210> SEQ ID NO 12
<211> LENGTH: 65
<212> TYPE: PRT
<213> ORGANISM: Artificial Sequence
<220> FEATURE:
<223> OTHER INFORMATION: modified hirudin

<400> SEQUENCE: 12

```
Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Arg Lys Gly Ser
             20                  25                  30

Asp Gly Glu Lys Asn Gln Cys Val Thr Gly Glu Gly Thr Pro Lys Pro
         35                  40                  45

Glu Ser His Asn Glu Gly Asp Phe Glu Glu Ile Pro Glu Glu Tyr Leu
     50                  55                  60

Gln
65
```

<210> SEQ ID NO 13
<211> LENGTH: 65
<212> TYPE: PRT
<213> ORGANISM: Artificial Sequence
<220> FEATURE:
<223> OTHER INFORMATION: modified hirudin

<400> SEQUENCE: 13

```
Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Arg Lys Gly Ser
             20                  25                  30

Asp Gly Glu Lys Asn Gln Cys Val Thr Gly Glu Gly Thr Pro Lys Pro
         35                  40                  45

Glu Ser His Asn Asn Gly Asp Phe Glu Glu Ile Pro Glu Glu Tyr Leu
     50                  55                  60

Gln
65
```

<210> SEQ ID NO 14

<211> LENGTH: 65
<212> TYPE: PRT
<213> ORGANISM: Artificial Sequence
<220> FEATURE:
<223> OTHER INFORMATION: modified hirudin

<400> SEQUENCE: 14

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Arg Arg Gly Ser
            20                  25                  30

Asp Gly Glu Lys Asn Gln Cys Thr Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 15
<211> LENGTH: 65
<212> TYPE: PRT
<213> ORGANISM: Artificial Sequence
<220> FEATURE:
<223> OTHER INFORMATION: modified hirudin

<400> SEQUENCE: 15

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ala Lys Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 16
<211> LENGTH: 65
<212> TYPE: PRT
<213> ORGANISM: Artificial Sequence
<220> FEATURE:
<223> OTHER INFORMATION: modified hirudin

<400> SEQUENCE: 16

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ala Gln Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 17
<211> LENGTH: 65
<212> TYPE: PRT
<213> ORGANISM: Artificial Sequence
<220> FEATURE:

<223> OTHER INFORMATION: modified hirudin

<400> SEQUENCE: 17

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ala Arg Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 18
<211> LENGTH: 65
<212> TYPE: PRT
<213> ORGANISM: Artificial Sequence
<220> FEATURE:
<223> OTHER INFORMATION: modified hirudin

<400> SEQUENCE: 18

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ala Thr Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 19
<211> LENGTH: 65
<212> TYPE: PRT
<213> ORGANISM: Artificial Sequence
<220> FEATURE:
<223> OTHER INFORMATION: modified hirudin

<400> SEQUENCE: 19

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Asp Ala Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 20
<211> LENGTH: 65
<212> TYPE: PRT
<213> ORGANISM: Artificial Sequence
<220> FEATURE:
<223> OTHER INFORMATION: modified hirudin

<400> SEQUENCE: 20

```
Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Asp Gln Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 21
<211> LENGTH: 65
<212> TYPE: PRT
<213> ORGANISM: Artificial Sequence
<220> FEATURE:
<223> OTHER INFORMATION: modified hirudin

<400> SEQUENCE: 21

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Asp Arg Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 22
<211> LENGTH: 65
<212> TYPE: PRT
<213> ORGANISM: Artificial Sequence
<220> FEATURE:
<223> OTHER INFORMATION: modified hirudin

<400> SEQUENCE: 22

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Glu Lys Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 23
<211> LENGTH: 65
<212> TYPE: PRT
<213> ORGANISM: Artificial Sequence
<220> FEATURE:
<223> OTHER INFORMATION: modified hirudin

<400> SEQUENCE: 23

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Glu Gln Gly Ser
```

-continued

```
                20                  25                  30
Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 24
<211> LENGTH: 65
<212> TYPE: PRT
<213> ORGANISM: Artificial Sequence
<220> FEATURE:
<223> OTHER INFORMATION: modified hirudin

<400> SEQUENCE: 24

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Glu Arg Gly Ser
                20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 25
<211> LENGTH: 65
<212> TYPE: PRT
<213> ORGANISM: Artificial Sequence
<220> FEATURE:
<223> OTHER INFORMATION: modified hirudin

<400> SEQUENCE: 25

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Glu Thr Gly Ser
                20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 26
<211> LENGTH: 65
<212> TYPE: PRT
<213> ORGANISM: Artificial Sequence
<220> FEATURE:
<223> OTHER INFORMATION: modified hirudin

<400> SEQUENCE: 26

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Arg Lys Gly Ser
                20                  25                  30

Asp Gly Glu Lys Asn Gln Cys Val Thr Gly Glu Gly Thr Pro Lys Pro
        35                  40                  45
```

```
Glu Ser His Asn Asp Gly Asp Phe Glu Glu Ile Pro Glu Glu Tyr Leu
    50                  55                  60

Gln
65

<210> SEQ ID NO 27
<211> LENGTH: 65
<212> TYPE: PRT
<213> ORGANISM: Artificial Sequence
<220> FEATURE:
<223> OTHER INFORMATION: modified hirudin

<400> SEQUENCE: 27

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Arg Gln Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 28
<211> LENGTH: 65
<212> TYPE: PRT
<213> ORGANISM: Artificial Sequence
<220> FEATURE:
<223> OTHER INFORMATION: modified hirudin

<400> SEQUENCE: 28

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Arg Arg Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 29
<211> LENGTH: 65
<212> TYPE: PRT
<213> ORGANISM: Artificial Sequence
<220> FEATURE:
<223> OTHER INFORMATION: modified hirudin

<400> SEQUENCE: 29

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Arg Thr Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60
```

Gln
65

<210> SEQ ID NO 30
<211> LENGTH: 65
<212> TYPE: PRT
<213> ORGANISM: Artificial Sequence
<220> FEATURE:
<223> OTHER INFORMATION: modified hirudin

<400> SEQUENCE: 30

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ser Ala Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60

Gln
65

<210> SEQ ID NO 31
<211> LENGTH: 65
<212> TYPE: PRT
<213> ORGANISM: Artificial Sequence
<220> FEATURE:
<223> OTHER INFORMATION: modified hirudin

<400> SEQUENCE: 31

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ser Lys Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60

Gln
65

<210> SEQ ID NO 32
<211> LENGTH: 65
<212> TYPE: PRT
<213> ORGANISM: Artificial Sequence
<220> FEATURE:
<223> OTHER INFORMATION: modified hirudin

<400> SEQUENCE: 32

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ser Gln Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60

Gln
65

<210> SEQ ID NO 33
<211> LENGTH: 65
<212> TYPE: PRT
<213> ORGANISM: Artificial Sequence
<220> FEATURE:
<223> OTHER INFORMATION: modified hirudin

<400> SEQUENCE: 33

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ser Arg Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 34
<211> LENGTH: 65
<212> TYPE: PRT
<213> ORGANISM: Artificial Sequence
<220> FEATURE:
<223> OTHER INFORMATION: modified hirudin

<400> SEQUENCE: 34

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ser Thr Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 35
<211> LENGTH: 65
<212> TYPE: PRT
<213> ORGANISM: Artificial Sequence
<220> FEATURE:
<223> OTHER INFORMATION: modified hirudin

<400> SEQUENCE: 35

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Thr Ala Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 36
<211> LENGTH: 65
<212> TYPE: PRT
<213> ORGANISM: Artificial Sequence -continued

```
<220> FEATURE:
<223> OTHER INFORMATION: modified hirudin

<400> SEQUENCE: 36

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Thr Lys Gly Ser
             20                  25                  30

Asp Gly Glu Lys Asn Gln Cys Val Thr Gly Glu Gly Thr Pro Lys Pro
         35                  40                  45

Glu Ser His Asn Asp Gly Asp Phe Glu Glu Ile Pro Glu Glu Tyr Leu
     50                  55                  60

Gln
 65

<210> SEQ ID NO 37
<211> LENGTH: 65
<212> TYPE: PRT
<213> ORGANISM: Artificial Sequence
<220> FEATURE:
<223> OTHER INFORMATION: modified hirudin

<400> SEQUENCE: 37

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Thr Gln Gly Ser
             20                  25                  30

Asp Gly Glu Lys Asn Gln Cys Val Thr Gly Glu Gly Thr Pro Lys Pro
         35                  40                  45

Glu Ser His Asn Asp Gly Asp Phe Glu Glu Ile Pro Glu Glu Tyr Leu
     50                  55                  60

Gln
 65

<210> SEQ ID NO 38
<211> LENGTH: 65
<212> TYPE: PRT
<213> ORGANISM: Artificial Sequence
<220> FEATURE:
<223> OTHER INFORMATION: modified hirudin

<400> SEQUENCE: 38

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Thr Arg Gly Ser
             20                  25                  30

Asp Gly Glu Lys Asn Gln Cys Val Thr Gly Glu Gly Thr Pro Lys Pro
         35                  40                  45

Glu Ser His Asn Asp Gly Asp Phe Glu Glu Ile Pro Glu Glu Tyr Leu
     50                  55                  60

Gln
 65

<210> SEQ ID NO 39
<211> LENGTH: 65
<212> TYPE: PRT
<213> ORGANISM: Artificial Sequence
<220> FEATURE:
<223> OTHER INFORMATION: modified hirudin

<400> SEQUENCE: 39
```

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Thr Thr Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 40
<211> LENGTH: 65
<212> TYPE: PRT
<213> ORGANISM: Artificial Sequence
<220> FEATURE:
<223> OTHER INFORMATION: modified hirudin

<400> SEQUENCE: 40

Val Val Tyr Thr Asp Cys Thr Glu Ser Gly Gln Asn Thr Cys Leu Cys
1               5                   10                  15

Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 41
<211> LENGTH: 65
<212> TYPE: PRT
<213> ORGANISM: Artificial Sequence
<220> FEATURE:
<223> OTHER INFORMATION: modified hirudin

<400> SEQUENCE: 41

Val Val Tyr Thr Asp Cys Thr Glu Ser Gly Gln Asn Leu Cys Ala Cys
1               5                   10                  15

Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 42
<211> LENGTH: 65
<212> TYPE: PRT
<213> ORGANISM: Artificial Sequence
<220> FEATURE:
<223> OTHER INFORMATION: modified hirudin

<400> SEQUENCE: 42

Val Val Tyr Thr Asp Cys Thr Glu Ser Gly Gln Asn Leu Cys His Cys
1               5                   10                  15

```
Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60

Gln
65

<210> SEQ ID NO 43
<211> LENGTH: 65
<212> TYPE: PRT
<213> ORGANISM: Artificial Sequence
<220> FEATURE:
<223> OTHER INFORMATION: modified hirudin

<400> SEQUENCE: 43

Val Val Tyr Thr Asp Cys Thr Glu Ser Gly Gln Asn Leu Cys Gln Cys
 1               5                  10                  15

Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60

Gln
65

<210> SEQ ID NO 44
<211> LENGTH: 65
<212> TYPE: PRT
<213> ORGANISM: Artificial Sequence
<220> FEATURE:
<223> OTHER INFORMATION: modified hirudin

<400> SEQUENCE: 44

Val Val Tyr Thr Asp Cys Thr Glu Ser Gly Gln Asn Leu Cys Thr Cys
 1               5                  10                  15

Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60

Gln
65

<210> SEQ ID NO 45
<211> LENGTH: 65
<212> TYPE: PRT
<213> ORGANISM: Artificial Sequence
<220> FEATURE:
<223> OTHER INFORMATION: modified hirudin

<400> SEQUENCE: 45

Val Val Tyr Thr Asp Cys Thr Glu Ser Gly Gln Asn Leu Cys Leu Cys
 1               5                  10                  15

Glu Gly Ser Val Ala Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
```

```
                        35                  40                  45
Glu Ser His Asn Asp Gly Asp Phe Glu Glu Ile Pro Glu Glu Tyr Leu
    50                  55                  60

Gln
65

<210> SEQ ID NO 46
<211> LENGTH: 65
<212> TYPE: PRT
<213> ORGANISM: Artificial Sequence
<220> FEATURE:
<223> OTHER INFORMATION: modified hirudin

<400> SEQUENCE: 46

Val Val Tyr Thr Asp Cys Thr Glu Ser Gly Gln Asn Leu Cys Leu Cys
 1               5                  10                  15

Glu Gly Ser Val Gly Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 47
<211> LENGTH: 65
<212> TYPE: PRT
<213> ORGANISM: Artificial Sequence
<220> FEATURE:
<223> OTHER INFORMATION: modified hirudin

<400> SEQUENCE: 47

Val Val Tyr Thr Asp Cys Thr Glu Ser Gly Gln Asn Leu Cys Leu Cys
 1               5                  10                  15

Glu Gly Ser Val His Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60

Gln
65

<210> SEQ ID NO 48
<211> LENGTH: 65
<212> TYPE: PRT
<213> ORGANISM: Artificial Sequence
<220> FEATURE:
<223> OTHER INFORMATION: modified hirudin

<400> SEQUENCE: 48

Val Val Tyr Thr Asp Cys Thr Glu Ser Gly Gln Asn Leu Cys Leu Cys
 1               5                  10                  15

Glu Gly Ser Val Lys Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
    50                  55                  60
```

Gln
65

<210> SEQ ID NO 49
<211> LENGTH: 65
<212> TYPE: PRT
<213> ORGANISM: Artificial Sequence
<220> FEATURE:
<223> OTHER INFORMATION: modified hirudin

<400> SEQUENCE: 49

Val Val Tyr Thr Asp Cys Thr Glu Ser Gly Gln Asn Leu Cys Leu Cys
1               5                   10                  15

Glu Gly Ser Val Asn Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 50
<211> LENGTH: 65
<212> TYPE: PRT
<213> ORGANISM: Artificial Sequence
<220> FEATURE:
<223> OTHER INFORMATION: modified hirudin

<400> SEQUENCE: 50

Val Val Tyr Thr Asp Cys Thr Glu Ser Gly Gln Asn Leu Cys Leu Cys
1               5                   10                  15

Glu Gly Ser Val Pro Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 51
<211> LENGTH: 65
<212> TYPE: PRT
<213> ORGANISM: Artificial Sequence
<220> FEATURE:
<223> OTHER INFORMATION: modified hirudin

<400> SEQUENCE: 51

Val Val Tyr Thr Asp Cys Thr Glu Ser Gly Gln Asn Leu Cys Leu Cys
1               5                   10                  15

Glu Gly Ser Val Gln Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

-continued

<210> SEQ ID NO 52
<211> LENGTH: 65
<212> TYPE: PRT
<213> ORGANISM: Artificial Sequence
<220> FEATURE:
<223> OTHER INFORMATION: modified hirudin

<400> SEQUENCE: 52

Val Val Tyr Thr Asp Cys Thr Glu Ser Gly Gln Asn Leu Cys Leu Cys
1               5                   10                  15

Glu Gly Ser Val Arg Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 53
<211> LENGTH: 65
<212> TYPE: PRT
<213> ORGANISM: Artificial Sequence
<220> FEATURE:
<223> OTHER INFORMATION: modified hirudin

<400> SEQUENCE: 53

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ala Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 54
<211> LENGTH: 65
<212> TYPE: PRT
<213> ORGANISM: Artificial Sequence
<220> FEATURE:
<223> OTHER INFORMATION: modified hirudin

<400> SEQUENCE: 54

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Asp Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 55
<211> LENGTH: 65
<212> TYPE: PRT

<213> ORGANISM: Artificial Sequence
<220> FEATURE:
<223> OTHER INFORMATION: modified hirudin

<400> SEQUENCE: 55

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Glu Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 56
<211> LENGTH: 65
<212> TYPE: PRT
<213> ORGANISM: Artificial Sequence
<220> FEATURE:
<223> OTHER INFORMATION: modified hirudin

<400> SEQUENCE: 56

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Gly Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 57
<211> LENGTH: 65
<212> TYPE: PRT
<213> ORGANISM: Artificial Sequence
<220> FEATURE:
<223> OTHER INFORMATION: modified hirudin

<400> SEQUENCE: 57

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys His Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 58
<211> LENGTH: 65
<212> TYPE: PRT
<213> ORGANISM: Artificial Sequence
<220> FEATURE:
<223> OTHER INFORMATION: modified hirudin

<400> SEQUENCE: 58

```
Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Lys Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65
```

<210> SEQ ID NO 59
<211> LENGTH: 65
<212> TYPE: PRT
<213> ORGANISM: Artificial Sequence
<220> FEATURE:
<223> OTHER INFORMATION: modified hirudin

<400> SEQUENCE: 59

```
Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Asn Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65
```

<210> SEQ ID NO 60
<211> LENGTH: 65
<212> TYPE: PRT
<213> ORGANISM: Artificial Sequence
<220> FEATURE:
<223> OTHER INFORMATION: modified hirudin

<400> SEQUENCE: 60

```
Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Gln Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65
```

<210> SEQ ID NO 61
<211> LENGTH: 65
<212> TYPE: PRT
<213> ORGANISM: Artificial Sequence
<220> FEATURE:
<223> OTHER INFORMATION: modified hirudin

<400> SEQUENCE: 61

```
Val Val Tyr Thr Asp Cys Thr Glu Ser Gly Gln Asn Leu Cys Leu Cys
1               5                   10                  15
```

Glu Gly Ser Val Val Cys Gly Gln Gly Asn Lys Cys Arg Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 62
<211> LENGTH: 65
<212> TYPE: PRT
<213> ORGANISM: Artificial Sequence
<220> FEATURE:
<223> OTHER INFORMATION: modified hirudin

<400> SEQUENCE: 62

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ser Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 63
<211> LENGTH: 65
<212> TYPE: PRT
<213> ORGANISM: Artificial Sequence
<220> FEATURE:
<223> OTHER INFORMATION: modified hirudin

<400> SEQUENCE: 63

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Thr Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 64
<211> LENGTH: 65
<212> TYPE: PRT
<213> ORGANISM: Artificial Sequence
<220> FEATURE:
<223> OTHER INFORMATION: modified hirudin

<400> SEQUENCE: 64

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ile Ala Gly Ser
            20                  25                  30

```
Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 65
<211> LENGTH: 65
<212> TYPE: PRT
<213> ORGANISM: Artificial Sequence
<220> FEATURE:
<223> OTHER INFORMATION: modified hirudin

<400> SEQUENCE: 65

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ile Asp Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 66
<211> LENGTH: 65
<212> TYPE: PRT
<213> ORGANISM: Artificial Sequence
<220> FEATURE:
<223> OTHER INFORMATION: modified hirudin

<400> SEQUENCE: 66

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ile Glu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 67
<211> LENGTH: 65
<212> TYPE: PRT
<213> ORGANISM: Artificial Sequence
<220> FEATURE:
<223> OTHER INFORMATION: modified hirudin

<400> SEQUENCE: 67

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ile Gly Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
```

```
                    50                  55                  60
Gln
 65

<210> SEQ ID NO 68
<211> LENGTH: 65
<212> TYPE: PRT
<213> ORGANISM: Artificial Sequence
<220> FEATURE:
<223> OTHER INFORMATION: modified hirudin

<400> SEQUENCE: 68

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ile His Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60
Gln
 65

<210> SEQ ID NO 69
<211> LENGTH: 65
<212> TYPE: PRT
<213> ORGANISM: Artificial Sequence
<220> FEATURE:
<223> OTHER INFORMATION: modified hirudin

<400> SEQUENCE: 69

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ile Lys Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60
Gln
 65

<210> SEQ ID NO 70
<211> LENGTH: 65
<212> TYPE: PRT
<213> ORGANISM: Artificial Sequence
<220> FEATURE:
<223> OTHER INFORMATION: modified hirudin

<400> SEQUENCE: 70

Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ile Asn Gly Ser
                20                  25                  30

Asp Gly Glu Lys Asn Gln Cys Val Thr Gly Glu Gly Thr Pro Lys Pro
            35                  40                  45

Glu Ser His Asn Asp Gly Asp Phe Glu Glu Ile Pro Glu Glu Tyr Leu
        50                  55                  60
Gln
 65
```

<210> SEQ ID NO 71
<211> LENGTH: 65
<212> TYPE: PRT
<213> ORGANISM: Artificial Sequence
<220> FEATURE:
<223> OTHER INFORMATION: modified hirudin

<400> SEQUENCE: 71

```
Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ile Pro Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65
```

<210> SEQ ID NO 72
<211> LENGTH: 65
<212> TYPE: PRT
<213> ORGANISM: Artificial Sequence
<220> FEATURE:
<223> OTHER INFORMATION: modified hirudin

<400> SEQUENCE: 72

```
Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ile Gln Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65
```

<210> SEQ ID NO 73
<211> LENGTH: 65
<212> TYPE: PRT
<213> ORGANISM: Artificial Sequence
<220> FEATURE:
<223> OTHER INFORMATION: modified hirudin

<400> SEQUENCE: 73

```
Val Val Tyr Thr Asp Cys Thr Glu Ser Gly Gln Asn Leu Cys Leu Cys
 1               5                  10                  15

Glu Gly Ser Val Val Cys Gly Gln Gly Asn Lys Cys Ile Arg Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65
```

<210> SEQ ID NO 74
<211> LENGTH: 65

```
<212> TYPE: PRT
<213> ORGANISM: Artificial Sequence
<220> FEATURE:
<223> OTHER INFORMATION: modified hirudin

<400> SEQUENCE: 74

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Ile Ser Gly Ser
             20                  25                  30

Asp Gly Glu Lys Asn Gln Cys Val Thr Gly Glu Gly Thr Pro Lys Pro
         35                  40                  45

Glu Ser His Asn Asp Gly Asp Phe Glu Glu Ile Pro Glu Glu Tyr Leu
     50                  55                  60

Gln
 65

<210> SEQ ID NO 75
<211> LENGTH: 65
<212> TYPE: PRT
<213> ORGANISM: Artificial Sequence
<220> FEATURE:
<223> OTHER INFORMATION: modified hirudin

<400> SEQUENCE: 75

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Ile Thr Gly Ser
             20                  25                  30

Asp Gly Glu Lys Asn Gln Cys Val Thr Gly Glu Gly Thr Pro Lys Pro
         35                  40                  45

Glu Ser His Asn Asp Gly Asp Phe Glu Glu Ile Pro Glu Glu Tyr Leu
     50                  55                  60

Gln
 65

<210> SEQ ID NO 76
<211> LENGTH: 65
<212> TYPE: PRT
<213> ORGANISM: Artificial Sequence
<220> FEATURE:
<223> OTHER INFORMATION: modified hirudin

<400> SEQUENCE: 76

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Ile Leu Gly Ser
             20                  25                  30

Asp Gly Glu Lys Asn Gln Cys Ala Thr Gly Glu Gly Thr Pro Lys Pro
         35                  40                  45

Glu Ser His Asn Asp Gly Asp Phe Glu Glu Ile Pro Glu Glu Tyr Leu
     50                  55                  60

Gln
 65

<210> SEQ ID NO 77
<211> LENGTH: 65
<212> TYPE: PRT
<213> ORGANISM: Artificial Sequence
<220> FEATURE:
<223> OTHER INFORMATION: modified hirudin
```

<400> SEQUENCE: 77

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ile Leu Gly Ser
            20                  25                  30

Asp Gly Glu Lys Asn Gln Cys Thr Thr Gly Glu Gly Thr Pro Lys Pro
        35                  40                  45

Glu Ser His Asn Asp Gly Asp Phe Glu Glu Ile Pro Glu Glu Tyr Leu
    50                  55                  60

Gln
65

<210> SEQ ID NO 78
<211> LENGTH: 65
<212> TYPE: PRT
<213> ORGANISM: Artificial Sequence
<220> FEATURE:
<223> OTHER INFORMATION: modified hirudin

<400> SEQUENCE: 78

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Thr Pro
        35                  40                  45

Glu Ser His Asn Asp Gly Asp Phe Glu Glu Ile Pro Glu Glu Tyr Leu
    50                  55                  60

Gln
65

<210> SEQ ID NO 79
<211> LENGTH: 65
<212> TYPE: PRT
<213> ORGANISM: Artificial Sequence
<220> FEATURE:
<223> OTHER INFORMATION: modified hirudin

<400> SEQUENCE: 79

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Ala
        35                  40                  45

Glu Ser His Asn Asp Gly Asp Phe Glu Glu Ile Pro Glu Glu Tyr Leu
    50                  55                  60

Gln
65

<210> SEQ ID NO 80
<211> LENGTH: 65
<212> TYPE: PRT
<213> ORGANISM: Artificial Sequence
<220> FEATURE:
<223> OTHER INFORMATION: modified hirudin

<400> SEQUENCE: 80

Val Val Tyr Thr Asp Cys Thr Glu Ser Gly Gln Asn Leu Cys Leu Cys

```
                 1               5                  10                 15
Glu Gly Ser Val Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Thr
            35                  40                  45

Glu Ser His Asn Asp Gly Asp Phe Glu Glu Ile Pro Glu Glu Tyr Leu
        50                  55                  60

Gln
65

<210> SEQ ID NO 81
<211> LENGTH: 65
<212> TYPE: PRT
<213> ORGANISM: Artificial Sequence
<220> FEATURE:
<223> OTHER INFORMATION: modified hirudin

<400> SEQUENCE: 81

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Glu Ser His Asn Glu Gly Asp Phe Glu Glu Ile Pro Glu Glu Tyr Leu
        50                  55                  60

Gln
65

<210> SEQ ID NO 82
<211> LENGTH: 65
<212> TYPE: PRT
<213> ORGANISM: Artificial Sequence
<220> FEATURE:
<223> OTHER INFORMATION: modified hirudin

<400> SEQUENCE: 82

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Glu Ser His Asn Asn Gly Asp Phe Glu Glu Ile Pro Glu Glu Tyr Leu
        50                  55                  60

Gln
65

<210> SEQ ID NO 83
<211> LENGTH: 65
<212> TYPE: PRT
<213> ORGANISM: Artificial Sequence
<220> FEATURE:
<223> OTHER INFORMATION: modified hirudin

<400> SEQUENCE: 83

Val Val Tyr Thr Asp Cys Thr Glu Ser Gly Gln Asn Leu Cys Leu Cys
  1               5                  10                  15

Glu Gly Ser Val Val Cys Gly Gln Gly Asn Lys Cys Ile Leu Gly Ser
                20                  25                  30
```

```
Asp Gly Glu Lys Asn Gln Cys Val Thr Gly Glu Gly Thr Pro Lys Pro
        35                  40                  45

Glu Ser His Asn Arg Gly Asp Phe Glu Glu Ile Pro Glu Glu Tyr Leu
    50                  55                  60

Gln
65

<210> SEQ ID NO 84
<211> LENGTH: 65
<212> TYPE: PRT
<213> ORGANISM: Artificial Sequence
<220> FEATURE:
<223> OTHER INFORMATION: modified hirudin

<400> SEQUENCE: 84

Val Val Tyr Thr Asp Cys Thr Glu Ser Gly Gln Asn Leu Cys Leu Cys
1               5                   10                  15

Glu Gly Ser Val Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Glu Ser His Asn Asp Gly Asp His Glu Glu Ile Pro Glu Glu Tyr Leu
    50                  55                  60

Gln
65

<210> SEQ ID NO 85
<211> LENGTH: 20
<212> TYPE: PRT
<213> ORGANISM: Artificial Sequence
<220> FEATURE:
<223> OTHER INFORMATION: secretion signal

<400> SEQUENCE: 85

Met Phe Ser Leu Lys Leu Phe Val Val Phe Leu Ala Val Cys Ile Cys
1               5                   10                  15

Val Ser Gln Ala
            20

<210> SEQ ID NO 86
<211> LENGTH: 20
<212> TYPE: PRT
<213> ORGANISM: Artificial Sequence
<220> FEATURE:
<223> OTHER INFORMATION: secretion signal

<400> SEQUENCE: 86

Met Val Ser Leu Lys Leu Phe Val Val Phe Leu Ala Val Cys Ile Cys
1               5                   10                  15

Val Ser Gln Ala
            20

<210> SEQ ID NO 87
<211> LENGTH: 15
<212> TYPE: PRT
<213> ORGANISM: hirudo medicinalis

<400> SEQUENCE: 87

Val Val Tyr Thr Asp Cys Thr Glu Ser Gly Gln Asn Leu Cys Leu
1               5                   10                  15
```

```
<210> SEQ ID NO 88
<211> LENGTH: 15
<212> TYPE: PRT
<213> ORGANISM: hirudo medicinalis

<400> SEQUENCE: 88

Leu Thr Tyr Thr Asp Cys Thr Glu Ser Gly Gln Asn Leu Cys Leu
1               5                   10                  15

<210> SEQ ID NO 89
<211> LENGTH: 15
<212> TYPE: PRT
<213> ORGANISM: hirudo medicinalis

<400> SEQUENCE: 89

Thr Asp Cys Thr Glu Ser Gly Gln Asn Leu Cys Leu Cys Glu Gly
1               5                   10                  15

<210> SEQ ID NO 90
<211> LENGTH: 15
<212> TYPE: PRT
<213> ORGANISM: hirudo medicinalis

<400> SEQUENCE: 90

Thr Glu Ser Gly Gln Asn Leu Cys Leu Cys Glu Gly Ser Asn Val
1               5                   10                  15

<210> SEQ ID NO 91
<211> LENGTH: 15
<212> TYPE: PRT
<213> ORGANISM: hirudo medicinalis

<400> SEQUENCE: 91

Gly Gln Asn Leu Cys Leu Cys Glu Gly Ser Asn Val Cys Gly Gln
1               5                   10                  15

<210> SEQ ID NO 92
<211> LENGTH: 15
<212> TYPE: PRT
<213> ORGANISM: hirudo medicinalis

<400> SEQUENCE: 92

Leu Cys Leu Cys Glu Gly Ser Asn Val Cys Gly Gln Gly Asn Lys
1               5                   10                  15

<210> SEQ ID NO 93
<211> LENGTH: 15
<212> TYPE: PRT
<213> ORGANISM: hirudo medicinalis

<400> SEQUENCE: 93

Cys Glu Gly Ser Asn Val Cys Gly Gln Gly Asn Lys Cys Ile Leu
1               5                   10                  15

<210> SEQ ID NO 94
<211> LENGTH: 15
<212> TYPE: PRT
<213> ORGANISM: hirudo medicinalis

<400> SEQUENCE: 94

Ser Asn Val Cys Gly Gln Gly Asn Lys Cys Ile Leu Gly Ser Asp
1               5                   10                  15

<210> SEQ ID NO 95
<211> LENGTH: 15
```

```
<212> TYPE: PRT
<213> ORGANISM: hirudo medicinalis

<400> SEQUENCE: 95

Cys Gly Gln Gly Asn Lys Cys Ile Leu Gly Ser Asp Gly Glu Lys
 1               5                  10                  15

<210> SEQ ID NO 96
<211> LENGTH: 15
<212> TYPE: PRT
<213> ORGANISM: hirudo medicinalis

<400> SEQUENCE: 96

Gly Asn Lys Cys Ile Leu Gly Ser Asp Gly Glu Lys Asn Gln Cys
 1               5                  10                  15

<210> SEQ ID NO 97
<211> LENGTH: 15
<212> TYPE: PRT
<213> ORGANISM: hirudo medicinalis

<400> SEQUENCE: 97

Cys Ile Leu Gly Ser Asp Gly Glu Lys Asn Gln Cys Val Thr Gly
 1               5                  10                  15

<210> SEQ ID NO 98
<211> LENGTH: 15
<212> TYPE: PRT
<213> ORGANISM: hirudo medicinalis

<400> SEQUENCE: 98

Gly Ser Asp Gly Glu Lys Asn Gln Cys Val Thr Gly Glu Gly Thr
 1               5                  10                  15

<210> SEQ ID NO 99
<211> LENGTH: 15
<212> TYPE: PRT
<213> ORGANISM: hirudo medicinalis

<400> SEQUENCE: 99

Gly Glu Lys Asn Gln Cys Val Thr Gly Glu Gly Thr Pro Lys Pro
 1               5                  10                  15

<210> SEQ ID NO 100
<211> LENGTH: 15
<212> TYPE: PRT
<213> ORGANISM: hirudo medicinalis

<400> SEQUENCE: 100

Asn Gln Cys Val Thr Gly Glu Gly Thr Pro Lys Pro Glu Ser His
 1               5                  10                  15

<210> SEQ ID NO 101
<211> LENGTH: 15
<212> TYPE: PRT
<213> ORGANISM: hirudo medicinalis

<400> SEQUENCE: 101

Val Thr Gly Glu Gly Thr Pro Lys Pro Glu Ser His Asn Asp Gly
 1               5                  10                  15

<210> SEQ ID NO 102
<211> LENGTH: 15
<212> TYPE: PRT
<213> ORGANISM: hirudo medicinalis
```

<400> SEQUENCE: 102

Glu Gly Thr Pro Lys Pro Glu Ser His Asn Asp Gly Asp Phe Glu
1 5 10 15

<210> SEQ ID NO 103
<211> LENGTH: 15
<212> TYPE: PRT
<213> ORGANISM: hirudo medicinalis

<400> SEQUENCE: 103

Pro Lys Pro Glu Ser His Asn Asp Gly Asp Phe Glu Glu Ile Pro
1 5 10 15

<210> SEQ ID NO 104
<211> LENGTH: 15
<212> TYPE: PRT
<213> ORGANISM: hirudo medicinalis

<400> SEQUENCE: 104

Glu Ser His Asn Asp Gly Asp Phe Glu Glu Ile Pro Glu Glu Tyr
1 5 10 15

<210> SEQ ID NO 105
<211> LENGTH: 15
<212> TYPE: PRT
<213> ORGANISM: hirudo medicinalis

<400> SEQUENCE: 105

Asn Asp Gly Asp Phe Glu Glu Ile Pro Glu Glu Tyr Tyr Leu Gln
1 5 10 15

<210> SEQ ID NO 106
<211> LENGTH: 15
<212> TYPE: PRT
<213> ORGANISM: Artificial Sequence
<220> FEATURE:
<223> OTHER INFORMATION: modified hirudin sequence

<400> SEQUENCE: 106

Cys Ala Ala Gly Ser Asp Gly Glu Lys Asn Gln Cys Val Thr Gly
1 5 10 15

<210> SEQ ID NO 107
<211> LENGTH: 15
<212> TYPE: PRT
<213> ORGANISM: Artificial Sequence
<220> FEATURE:
<223> OTHER INFORMATION: modified hirudin sequence

<400> SEQUENCE: 107

Cys Glu Lys Gly Ser Asp Gly Glu Lys Asn Gln Cys Val Thr Gly
1 5 10 15

<210> SEQ ID NO 108
<211> LENGTH: 15
<212> TYPE: PRT
<213> ORGANISM: Artificial Sequence
<220> FEATURE:
<223> OTHER INFORMATION: modified hirudin sequence

<400> SEQUENCE: 108

Cys Arg His Gly Ser Asp Gly Glu Lys Asn Gln Cys Val Thr Gly
1 5 10 15